(12) United States Patent
Mueth et al.

(10) Patent No.: US 8,158,927 B2
(45) Date of Patent: Apr. 17, 2012

(54) MULTIPLE LAMINAR FLOW-BASED PARTICLE AND CELLULAR SEPARATION WITH LASER STEERING

(75) Inventors: Daniel Mueth, Chicago, IL (US); Joseph Plewa, Park Ridge, IL (US); Jessica Shireman, Kansas City, MO (US); Amy Anderson, Palatine, IL (US); Lewis Gruber, Chicago, IL (US); Neil Harris Rosenbaum, Chicago, IL (US)

(73) Assignee: Arryx, Inc., Chicago, IL (US)

( * ) Notice: Subject to any disclaimer, the term of this patent is extended or adjusted under 35 U.S.C. 154(b) by 85 days.

(21) Appl. No.: 12/659,277

(22) Filed: Mar. 2, 2010

(65) Prior Publication Data
US 2010/0216208 A1 Aug. 26, 2010

Related U.S. Application Data

(60) Division of application No. 12/213,109, filed on Jun. 13, 2008, now Pat. No. 7,699,767, which is a division of application No. 11/543,773, filed on Oct. 6, 2006, now Pat. No. 7,402,131, which is a division of application No. 10/934,597, filed on Sep. 3, 2004, now Pat. No. 7,118,676, which is a continuation-in-part of application No. 10/867,328, filed on Jun. 13, 2004, now Pat. No. 7,150,834, which is a continuation-in-part of application No. 10/630,904, filed on Jul. 31, 2003, now Pat. No. 7,241,988.

(60) Provisional application No. 60/399,386, filed on Jul. 31, 2002, provisional application No. 60/435,541, filed on Dec. 20, 2002, provisional application No. 60/571,141, filed on May 14, 2004, provisional application No. 60/499,957, filed on Sep. 4, 2003, provisional application No. 60/511,458, filed on Oct. 15, 2003.

(51) Int. Cl.
*B01D 21/01* (2006.01)

(52) U.S. Cl. ......... 250/251; 494/36; 494/45; 435/173.1; 210/732; 210/800; 210/802

(58) Field of Classification Search ................. 250/251; 494/36, 45; 435/173.1, 173.9, 283.1, 308.1; 210/732, 800, 802
See application file for complete search history.

(56) References Cited

U.S. PATENT DOCUMENTS
3,649,829 A 3/1972 Randolph
(Continued)

FOREIGN PATENT DOCUMENTS
DE 19952322 5/2001
(Continued)

OTHER PUBLICATIONS
Hori M et al. "Cell fusion by optical trapping with laser—involves contacting different cells . . . " WPI/Thomson, Dec. 27, 1991 Abstract.
(Continued)

*Primary Examiner* — Kiet T Nguyen
(74) *Attorney, Agent, or Firm* — Jean C. Edwards, Esq.; Edwards Neils PLLC

(57) ABSTRACT

The invention provides a method, apparatus and system for separating blood and other types of cellular components, and can be combined with holographic optical trapping manipulation or other forms of optical tweezing. One of the exemplary methods includes providing a first flow having a plurality of blood components; providing a second flow; contacting the first flow with the second flow to provide a first separation region; and differentially sedimenting a first blood cellular component of the plurality of blood components into the second flow while concurrently maintaining a second blood cellular component of the plurality of blood components in the first flow. The second flow having the first blood cellular component is then differentially removed from the first flow having the second blood cellular component. Holographic optical traps may also be utilized in conjunction with the various flows to move selected components from one flow to another, as part of or in addition to a separation stage.

13 Claims, 22 Drawing Sheets

U.S. PATENT DOCUMENTS

| | | | |
|---|---|---|---|
| 3,960,449 | A | 6/1976 | Carleton et al. |
| 4,325,706 | A | 4/1982 | Gershman et al. |
| 4,409,106 | A | 10/1983 | Furuta et al. |
| 4,424,132 | A | 1/1984 | Iriguchi |
| 4,660,971 | A | 4/1987 | Sage et al. |
| 4,667,830 | A | 5/1987 | Nozaki et al. |
| 5,007,732 | A | 4/1991 | Ohki et al. |
| 5,100,627 | A | 3/1992 | Buican et al. |
| 5,180,065 | A | 1/1993 | Touge et al. |
| 5,194,909 | A | 3/1993 | Tycko |
| 5,229,297 | A | 7/1993 | Schnipelsky et al. |
| 5,483,469 | A | 1/1996 | Van den Engh et al. |
| 5,620,857 | A | 4/1997 | Weetall et al. |
| 5,674,743 | A | 10/1997 | Ulmer |
| 5,800,690 | A | 9/1998 | Chow et al. |
| 5,837,115 | A | 11/1998 | Austin et al. |
| 5,849,178 | A | 12/1998 | Holm et al. |
| 5,879,625 | A | 3/1999 | Roslaniec et al. |
| 5,966,457 | A | 10/1999 | Lemelson |
| 6,053,856 | A | 4/2000 | Hlavinka |
| 6,071,422 | A | 6/2000 | Hlavinka et al. |
| H1960 | H | 6/2001 | Conrad et al. |
| 6,368,871 | B1 | 4/2002 | Christel et al. |
| 6,416,190 | B1 | 7/2002 | Grier et al. |
| 6,432,630 | B1 | 8/2002 | Blankenstein |
| 6,451,264 | B1 | 9/2002 | Bhullar et al. |
| 6,506,609 | B1 | 1/2003 | Wada et al. |
| 6,524,860 | B1 | 2/2003 | Seidel et al. |
| 6,637,463 | B1 | 10/2003 | Lei et al. |
| 6,727,451 | B1 | 4/2004 | Fuhr et al. |
| 6,815,664 | B2 | 11/2004 | Wang et al. |
| 6,833,542 | B2 | 12/2004 | Wang et al. |
| 6,838,056 | B2 | 1/2005 | Foster |
| 6,944,324 | B2 | 9/2005 | Tran et al. |
| 7,029,430 | B2 | 4/2006 | Hlavinka et al. |
| 7,241,988 | B2 | 7/2007 | Gruber et al. |
| 7,482,577 | B2 * | 1/2009 | Gruber et al. ............ 250/251 |
| 2002/0058332 | A1 | 5/2002 | Quake et al. |
| 2002/0176069 | A1 | 11/2002 | Hansen et al. |
| 2003/0032204 | A1 | 2/2003 | Walt et al. |
| 2003/0047676 | A1 | 3/2003 | Grier et al. |
| 2003/0186426 | A1 | 10/2003 | Brewer et al. |
| 2005/0061962 | A1 | 3/2005 | Mueth et al. |
| 2005/0121604 | A1 | 6/2005 | Mueth et al. |
| 2006/0058167 | A1 | 3/2006 | Ragusa et al. |
| 2006/0152707 | A1 | 7/2006 | Kanda |

FOREIGN PATENT DOCUMENTS

| | | |
|---|---|---|
| EP | 0057907 | 8/1982 |
| EP | 0679325 | 11/1995 |
| FR | 2798557 | 3/2001 |
| JP | 57-131451 | 8/1982 |
| JP | 58-090513 | 5/1983 |
| JP | 06-327494 | 11/1994 |
| JP | 07-024309 | 1/1995 |
| JP | 2002-153260 | 5/2002 |
| JP | 2005-502482 | 1/2005 |
| WO | WO 99/39223 | 8/1999 |
| WO | WO 01/18400 | 3/2001 |
| WO | WO 2004/012133 | 2/2004 |

OTHER PUBLICATIONS

Paul O.P. TS'O, "Basic Principles in Nucleic Acid Chemistry", National Library of Medicine 1974, pp. 311-387, Academic Press Inc., New York, NY.

Stephen P. Smith et al., Inexpensive Optical Tweezers for Undergraduate Laboratories, Am. J. Phys. vol. 67, Jan. 1999.

S. Takayama et al., "Patterning cells and their environments using multiple laminar fluid flows . . ." Proc. Natl. Acad. Sci. USA, vol. 96, pp. 5545-5548, May 1999.

* cited by examiner

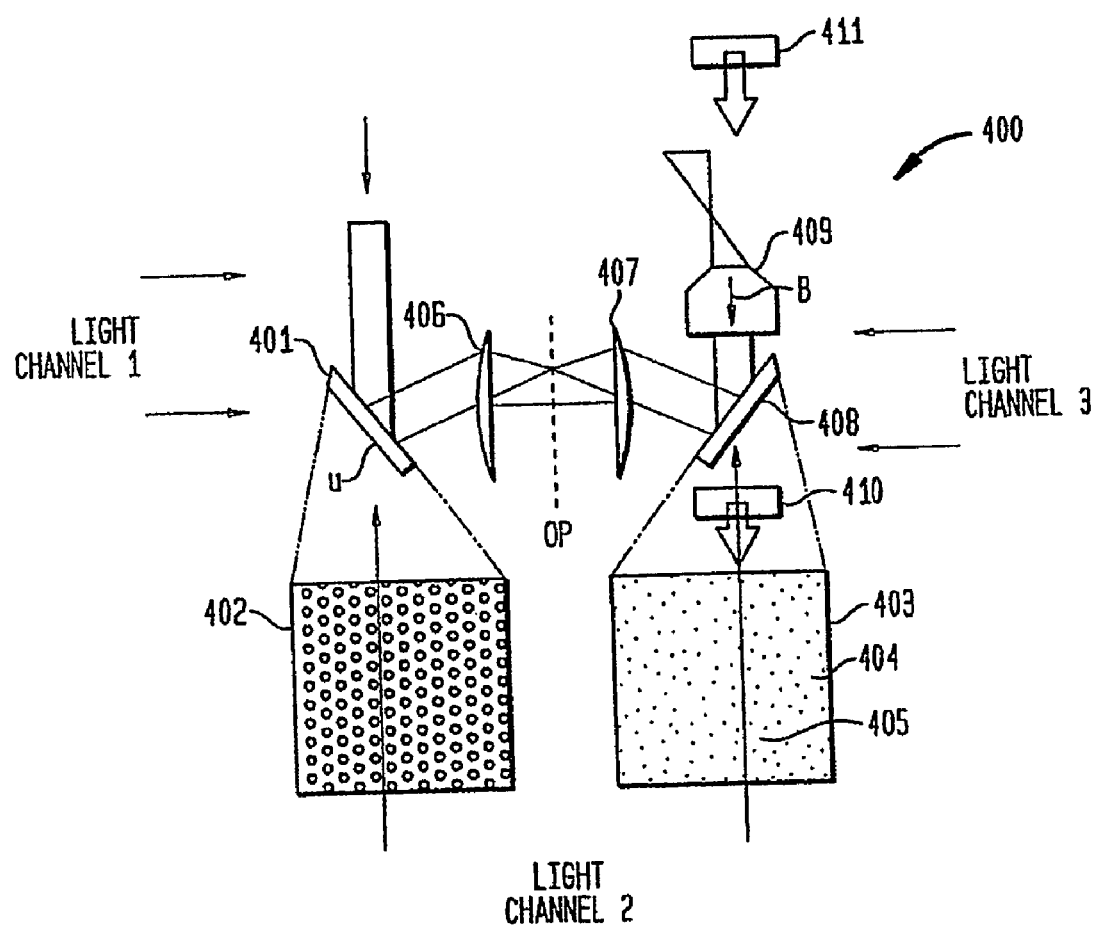

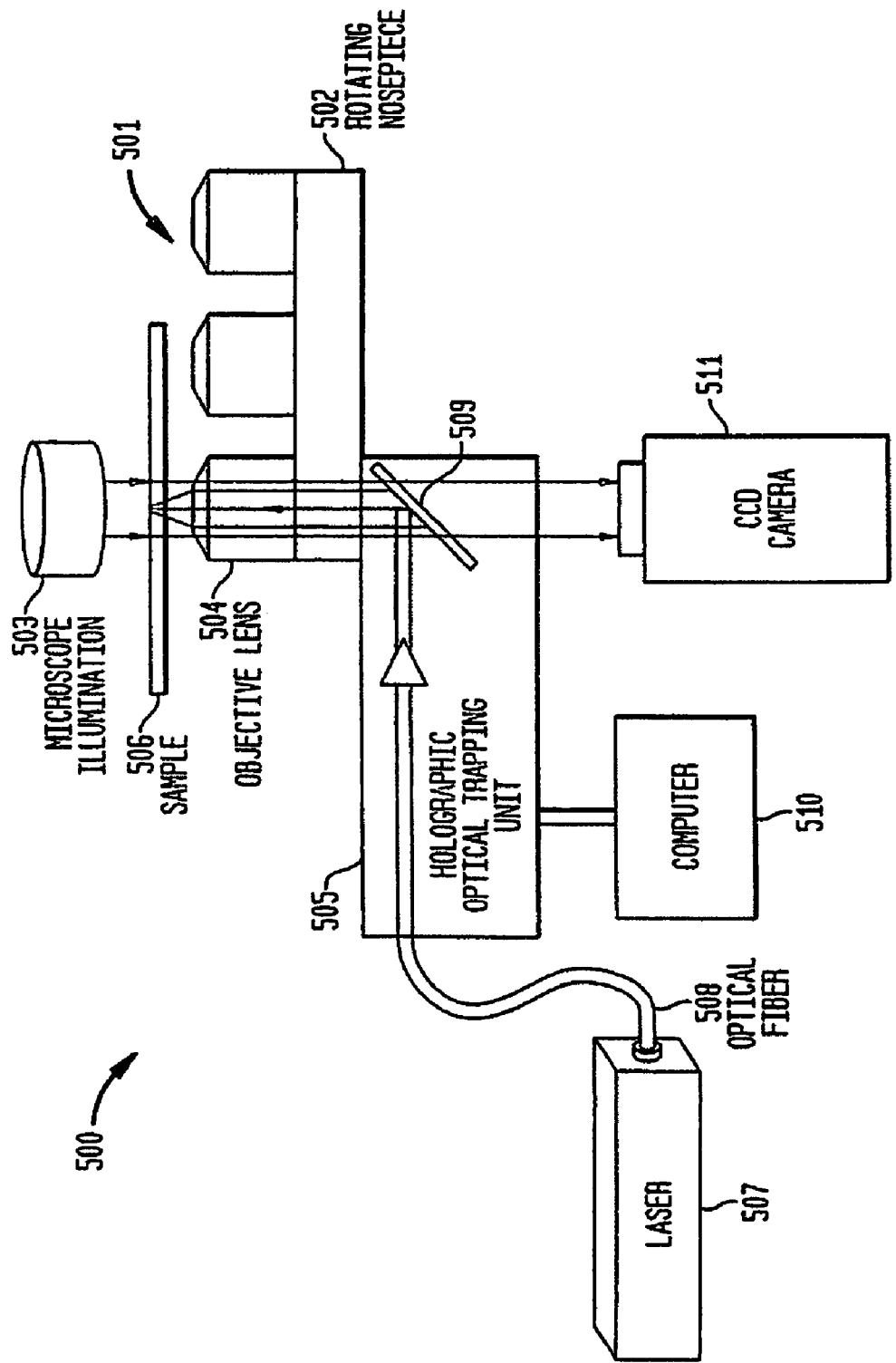

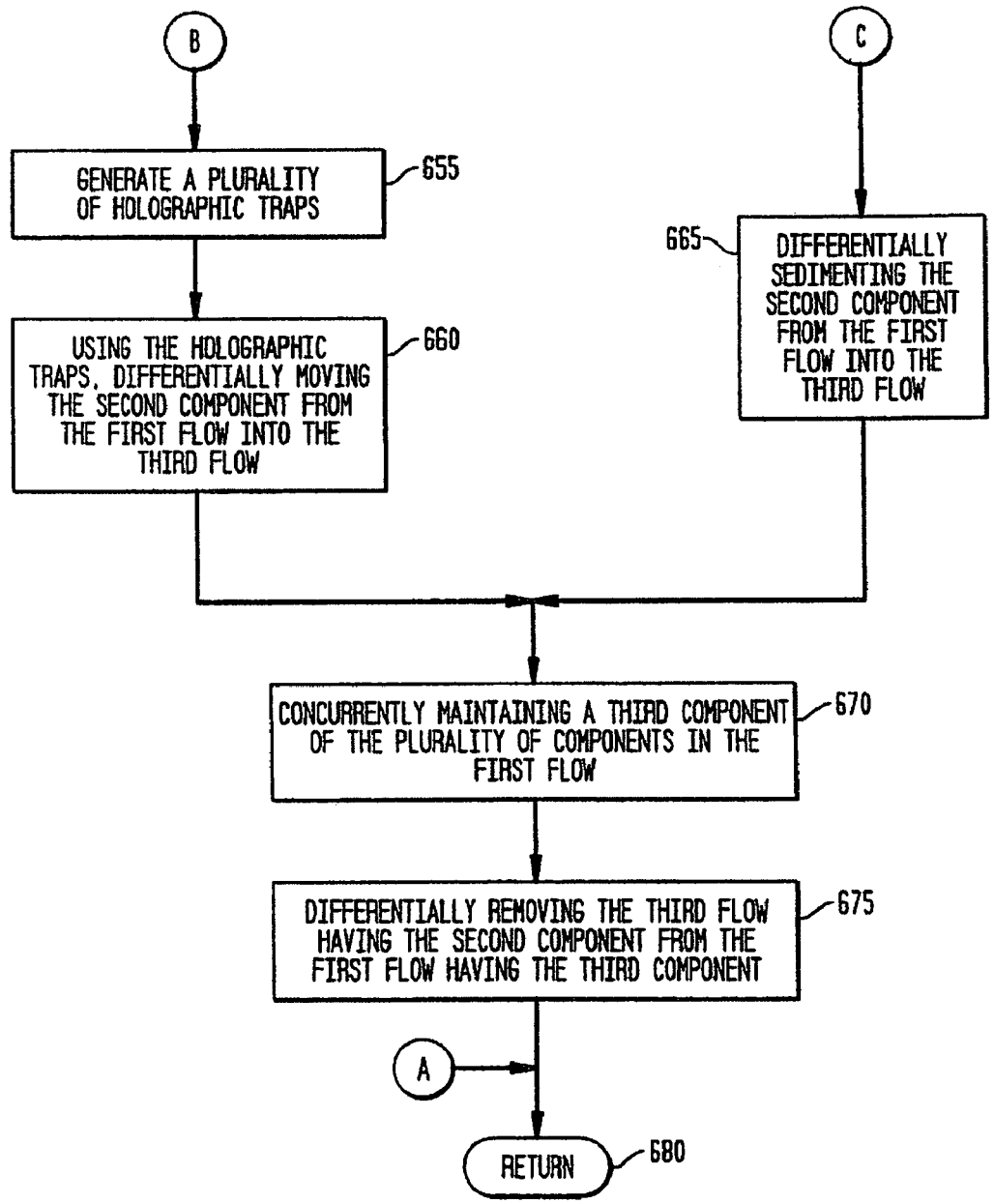

2200

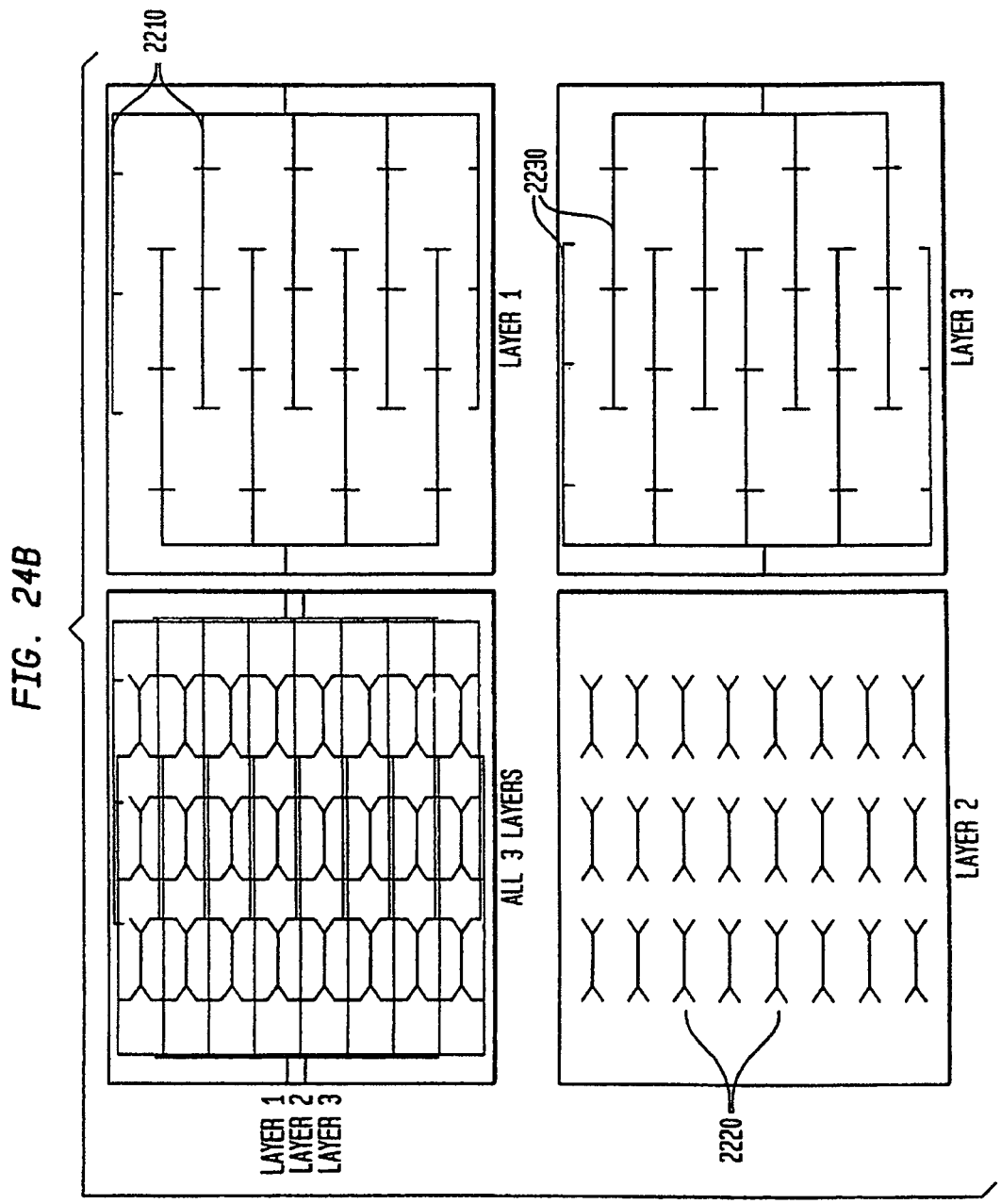

MULTIPLE LAMINAR FLOW-BASED PARTICLE AND CELLULAR SEPARATION WITH LASER STEERING

CROSS-REFERENCE TO RELATED APPLICATIONS AND PRIORITY CLAIMS

The present application is a divisional application of parent U.S. patent application Ser. No. 12/213,109, filed Jun. 13, 2008 now U.S. Pat. No. 7,699,767, which is a divisional application of U.S. patent application Ser. No. 11/543,773, filed Oct. 6, 2006, now U.S. Pat. No. 7,402,131, which is a divisional application of U.S. patent application Ser. No. 10/934,597, filed Sep. 3, 2004, now U.S. Pat. No. 7,118,676, which is a continuation-in-part of U.S. patent application Ser. No. 10/867,328, filed Jun. 13, 2004, now U.S. Pat. No. 7,150,834, which is a continuation-in-part of U.S. patent application Ser. No. 10/630,904, filed Jul. 31, 2003, now U.S. Pat. No. 7,241,988, and claims priority via U.S. patent application Ser. No. 10/630,904, to U.S. Provisional Patent Application No. 60/399,386, filed Jul. 31, 2002, and 60/435,541, filed Dec. 20, 2002, and claims priority via U.S. patent application Ser. No. 10/934,597 to U.S. Provisional Patent Application No. 60/571,141, filed May 14, 2004, U.S. Provisional Patent Application No. 60/499,957, filed Sep. 4, 2003, and U.S. Provisional Patent Application No. 60/511,458, filed Oct. 15, 2003, commonly assigned herewith, the contents of all of which are incorporated by reference herein, with priority claimed for all commonly disclosed subject matter.

The present invention is related to Jessica Shireman et al. U.S. Provisional Patent Application Ser. No. 60/571,141, filed May 14, 2004, entitled "System and Method of Sorting Blood Cells Using Holographic Laser Steering", commonly assigned herewith, the contents of which are incorporated by reference herein, with priority claimed for all commonly disclosed subject matter (the "second related application").

The present invention is related to and a conversion to a full utility application of Daniel M. Mueth, U.S. Patent Application Ser. No. 60/499,957, filed Sep. 4, 2003, entitled "Passive Fluidic Sorter", commonly assigned herewith, the contents of which are incorporated by reference herein, with priority claimed for all commonly disclosed subject matter (the "third related application").

The present invention is related to and a conversion to a full utility application of Daniel M. Mueth, U.S. Patent Application Ser. No. 60/511,458, filed Oct. 15, 2003, entitled "Passive Fluidic Sorter", commonly assigned herewith, the contents of which are incorporated by reference herein, with priority claimed for all commonly disclosed subject matter (the "fourth related application").

The present invention is related to Lewis Gruber et al., U.S. patent application Ser. No. 10/630,904, filed Jul. 31, 2003, entitled "System and Method of Sorting Materials Using Holographic Laser Steering", commonly assigned herewith, the contents of which are incorporated by reference herein, with priority claimed for all commonly disclosed subject matter (the "fifth related application").

FIELD OF THE INVENTION

The present invention relates generally to techniques and systems for separation of particulate or cellular materials such as blood, semen and other particles or cells into their various components and fractions, using multiple laminar flows which further may be coupled with laser steering such as holographic optical trapping and manipulation.

BACKGROUND OF THE INVENTION

There are several categories of blood cells. Erythrocyte or red blood cell (RBC) counts are for women 4.8 million cells/$\mu$l and men 5.4 million RBCs make up 93% of the solid element in blood and about 42% of blood volume. Platelets are 2 $\mu$m-3 $\mu$m in size. They represent 7% of the solid elements in blood and about 3% of the blood volume, corresponding to about 1.5 to $4\times10^{11}$ cells per liter. There are 5 general types of white blood cells (WBCs) or leukocytes accounting for about 1.5 to $4\times10^9$ cells per liter. The WBCs comprise: 50-70% Neutrophils (12-15 $\mu$m in size); 2-4% Eosinophils (12-15 $\mu$m in size); 0.5-1% Basophils (9-10 $\mu$m in size); 20-40% Lymphocytes (25% B-cells and 75% T-cells) (8-10 $\mu$m in size); and 3-8% Monocytes (16-20 $\mu$m in size). They comprise 0.16% of the solid elements in the blood, and approximately 0.1% of the blood volume corresponding to around 4 to $12\times10^9$ per liter. A subject with an infection might have a WBC count as high as $25\times10^9$ per liter.

Platelets are the smallest cells in the blood and are important for releasing proteins into the blood that are involved in clotting. Patients with immune diseases that cause lower counts (such as cancer, leukemia and other chemotherapy patients) sometimes need platelet transfusions to prevent their counts from becoming too low. The platelet count in adults is normally between 140,000-440,000 cells/$\mu$l, and this number should not fall below 50,000 cells/$\mu$L because platelets play an integral role in blood clotting.

Blood separation techniques have traditionally employed discrete centrifugation processes. More particularly, a certain volume of blood is removed from a donor at a particular time. That volume of blood is then subjected to different levels of centrifugation to provide corresponding blood fractions for blood components such as plasma, platelets, red blood cells, and white blood cells. This process is discrete, rather than continuous, such that if more blood from the donor is to be processed, another volume is removed from the donor, and the process is repeated.

The steps in platelet collection are: collection of blood from donor addition of anticoagulant; separation via centrifugation; return of red cells, leukocytes and plasma to the donor. A collection normally contains about 200-400 ml of plasma, which is reduced to avoid incompatibility. This collection normally contains about 8 to $8.5\times10^{10}$ platelets. A donor normally gives approximately 10% of his/her platelets with no loss in clotting ability, although a larger number of platelets could be separated from the blood. These platelets must be used within five days of collection.

Plateletpheresis, called apheresis, is a state of the art process by which platelets are separated [Haemonetics Component Collection System (CCS) and Multi Component System (Multi)(Haemonetics, Braintree, Mass.)]. This automated machine separates platelets from blood over a period of 1.5 to 2 hours (assuming 10% donation). This process is faster than traditional approaches and is completely automated and can be used for single or double platelet doses. Nevertheless, the process is slow relative to the patience of donors and is capable of improvement for the purity of the separated platelet fraction.

Other procedures are also time consuming, often taking several hours, particularly when unused blood fractions are to be returned to the donor. For example, platelet donation make take several hours, as whole blood is removed from the donor, fractionated through centrifugation to obtain the platelets, and the remaining blood components are then injected back into the donor. This centrifugation process is also comparatively harsh, also can result in damage to a proportion of the harvested cells, effectively reducing the usable yield of the blood fractions.

Other types of separations are also either time consuming or cannot process large volumes of material in a timely fashion. For example, sperm sorting, in which viable and motile sperm are isolated from non-viable or non-motile sperm, is often a time-consuming task, with severe volume restrictions.

As discussed below in greater detail in describing the present invention, manipulations of particles, such as that described in the second and fifth related applications, may also be part of a novel separation technique. One conventional technique in manipulating microscopic objects is optical trapping. An accepted description of the effect of optical trapping is that tightly focused light, such as light focused by a high numerical aperture microscope lens, has a steep intensity gradient. Optical traps use the gradient forces of a beam of light to trap a particle based on its dielectric constant.

To minimize its energy, a particle having a dielectric constant higher than the surrounding medium will move to the region of an optical trap where the electric field is the highest. Particles with at least a slight dielectric constant differential with their surroundings are sensitive to this gradient and are either attracted to or repelled from the point of highest light intensity, that is, to or from the light beam's focal point. In constructing an optical trap, optical gradient forces from a single beam of light are employed to manipulate the position of a dielectric particle immersed in a fluid medium with a refractive index smaller than that of the particle, but reflecting, absorbing and low dielectric constant particles may also be manipulated.

The optical gradient force in an optical trap competes with radiation pressure which tends to displace the trapped particle along the beam axis. An optical trap may be placed anywhere within the focal volume of an objective lens by appropriately selecting the input beam's propagation direction and degree of collimation. A collimated beam entering the back aperture of an objective lens comes to a focus in the center of the lens' focal plane while another beam entering at an angle comes to a focus off-center. A slightly diverging beam focuses downstream of the focal plane while a converging beam focuses upstream. Multiple beams entering the input pupil of the lens simultaneously each form an optical trap in the focal volume at a location determined by its angle of incidence. The holographic optical trapping technique uses a phase modifying diffractive optical element to impose the phase pattern for multiple beams onto the wavefront of a single input beam, thereby transforming the single beam into multiple traps.

Phase modulation of an input beam is preferred for creating optical traps because trapping relies on the intensities of beams and not on their relative phases. Amplitude modulations may divert light away from traps and diminish their effectiveness.

When a particle is optically trapped, optical gradient forces exerted by the trap exceed other radiation pressures arising from scattering and absorption. For a Gaussian $TEM_{00}$ input laser beam, this generally means that the beam diameter should substantially coincide with the diameter of the entrance pupil. A preferred minimum numerical aperture to form a trap is about 0.9 to about 1.0.

One difficulty in implementing optical trapping technology is that each trap to be generated generally requires its own focused beam of light. Many systems of interest require multiple optical traps, and several methods have been developed to achieve multiple trap configurations. One existing method uses a single light beam that is redirected between multiple trap locations to "time-share" the beam between various traps. However, as the number of traps increases, the intervals during which each trap is in its "off" state may become long for particles to diffuse away from the trap location before the trap is re-energized. All these concerns have limited implementations of this method to less than about 10 traps per system.

Another traditional method of creating multi-trap systems relies on simultaneously passing multiple beams of light through a single high numerical aperture lens. This is done by either using multiple lasers or by using one or more beam splitters in the beam of a single laser. One problem with this technique is that, as the number of traps increases, the optical system becomes progressively more and more complex. Because of these problems, the known implementations of this method are limited to less than about 5 traps per system.

In a third approach for achieving a multi-trap system, a diffractive optical element (DOE) (e.g., a phase shifting hologram utilizing either a transmission or a reflection geometry) is used to alter a single laser beam's wavefront. This invention is disclosed, in U.S. Pat. No. 6,055,106 to Grier et al. The wavefront is altered so that the downstream laser beam essentially becomes a large number of individual laser beams with relative positions and directions of travel fixed by the exact nature of the diffractive optical element. In effect, the Fourier transform of the DOE produces a set of intensity peaks each of which act as an individual trap or "tweezer."

Some implementations of the third approach have used a fixed transmission hologram to create between 16 and 400 individual trapping centers.

A fixed hologram has been used to demonstrate the principle of holographic optical trapping but using a liquid crystal grating as the hologram permitted 'manufacture' of a separate hologram for each new distribution of traps. The spatially varying phase modulation imposed on the trapping laser by the liquid crystal grating may be easily controlled in real time by a computer, thus permitting a variety of dynamic manipulations.

Other types of traps that may be used to optically trap particles include, but are not limited to, optical vortices, optical bottles, optical rotators and light cages. An optical vortex produces a gradient surrounding an area of zero electric field which is useful to manipulate particles with dielectric constants lower than the surrounding medium or which are reflective, or other types of particles which are repelled by an optical trap. To minimize its energy, such a particle will move to the region where the electric field is the lowest, namely the zero electric field area at the focal point of an appropriately shaped laser beam. The optical vortex provides an area of zero electric field much like the hole in a doughnut (toroid). The optical gradient is radial with the highest electric field at the circumference of the doughnut. The optical vortex detains a small particle within the hole of the doughnut. The detention is accomplished by slipping the vortex over the small particle along the line of zero electric field.

The optical bottle differs from an optical vortex in that it has a zero electric field only at the focus and a non-zero electric field in all other directions surrounding the focus, at an end of the vortex. An optical bottle may be useful in trapping atoms and nanoclusters which may be too small or too absorptive to trap with an optical vortex or optical tweezers. (See J. Arlt and M. J. Padgett. "Generation of a beam with a dark focus surrounded by regions of higher intensity: The optical bottle beam," Opt. Lett. 25, 191-193, 2000.)

The light cage (U.S. Pat. No. 5,939,716) is loosely, a macroscopic cousin of the optical vortex. A light cage forms a time-averaged ring of optical traps to surround a particle too large or reflective to be trapped with dielectric constants lower than the surrounding medium.

When the laser beam is directed through or reflected from the phase patterning optical element, the phase patterning optical element produces a plurality of beamlets having an altered phase profile. Depending on the number and type of optical traps desired, the alteration may include diffraction, wavefront shaping, phase shifting, steering, diverging and converging. Based upon the phase profile chosen, the phase patterning optical element may be used to generate optical traps in the form of optical traps, optical vortices, optical bottles, optical rotators, light cages, and combinations of two or more of these forms.

Researchers have sought indirect methods for manipulating cells, such as tagging the cells with diamond microparticles and then tweezing the diamond particles. Cell manipulations have included cell orientation for microscopic analysis as well as stretching cells. Tissue cells have also been arranged with tweezers in vitro in the same spatial distribution as in vivo.

In addition to the cells themselves, optical tweezers have been used to manipulate cellular organelles, such as vesicles transported along microtubules, chromosomes, or globular DNA. Objects have also been inserted into cells using optical tweezers.

Accordingly, as an example of new types of sorting using laser steered optical traps, a method of cell sorting using a technique which isolates valuable cells from other cells, tissues, and contaminants is needed. Further, a way of achieving a unique contribution of optical trapping to the major industrial needs of blood cell sorting and purification is required. Still further, there is a need to separate sperm cells in the animal husbandry market.

As a consequence, a need remains for a separation technique and apparatus which is continuous, has high throughput, provides time saving, and which causes negligible or minimal damage to the various components for separation. In addition, such techniques should have further applicability to biological or medical areas, such as for separations of blood, sperm, other cellular materials, as well as viral, cell organelle, globular structures, colloidal suspensions, and other biological materials.

SUMMARY OF THE INVENTION

The exemplary embodiments of the present invention provide for separating components in a mixture, such as separating the various blood components of whole blood into corresponding fractions, such as a platelet fraction, a red blood cell fraction, a white blood cell fraction, and a plasma fraction. The various embodiments of the present invention provide separation of components on a continuous basis, such as within a continuous, closed system, without the potential damage and contamination of prior art methods, particularly for fractionation of blood components. The continuous process of the present invention also provides significant time savings and higher throughput for blood fractionation. In addition, the various embodiments may also include additional means for separating and manipulating the components, particularly holographic optical manipulation and separation. The various embodiments may also be applied to separations of other types of cellular and biological materials, such as sperm, viruses, bacteria, cell debris, cell organelles, globular structures, colloidal suspensions, cellular debris, and other biological materials.

As used herein, "Particle" refers to a biological or other chemical material including, but not limited to, oligonucleotides, polynucleotides, chemical compounds, proteins, lipids, polysaccharides, ligands, cells, antibodies, antigens, cellular organelles, lipids, blastomeres, aggregations of cells, microorganisms, peptides, cDNA, RNA and the like.

An exemplary method of separating blood into components includes providing a first flow having a plurality of blood components; providing a second flow; contacting the first flow with the second flow to provide a first separation region; and differentially sedimenting a first blood cellular component of the plurality of blood components into the second flow while concurrently maintaining a second blood cellular component of the plurality of blood components in the first flow. The second flow having the first blood cellular component is then differentially removed from the first flow having the second blood cellular component.

The various sedimentation steps of the present invention may be rate zonal or isopycnic. In addition, the first flow and the second flow are substantially non-turbulent, and may also be substantially laminar.

In a selected embodiment, the first blood cellular component is a plurality of red blood cells and a plurality of white blood cells, and the second blood cellular component is a plurality of platelets. For the first blood cellular component, the plurality of white blood cells may be holographically separated (through laser steering) from the plurality of red blood cells. Other holographic manipulations of the present invention include holographically removing a plurality of contaminants from the first flow, holographically separating biological debris from the first flow, and holographically separating a plurality of second blood cellular components from the first flow.

Additional separation stages may also be included, with the exemplary method providing a third flow; contacting the first flow with the third flow to provide a second separation region; and differentially sedimenting the second blood cellular component of the plurality of blood components to sediment into the third flow while concurrently maintaining a third blood component of the plurality of blood components in the first flow. In selected embodiments, the second blood cellular component is a plurality of platelets and wherein the third blood component is plasma.

A plurality of separation stages may also be combined to form more complicated structures having multiple separation stages, connected in series, connected in parallel, or in combinations of both.

A second exemplary method of separating a fluid mixture into constituent, non-motile components, in accordance with the present invention, includes: providing a substantially laminar first flow having the fluid mixture, the fluid mixture having a plurality of components, the plurality of components having a corresponding plurality of sedimentation rates; providing a substantially laminar second flow; contacting the first flow with the second flow to provide a first separation region, the first flow and the second flow having a substantially non-turbulent interface within the separation region; differentially sedimenting from the first flow a first component of the plurality of components into the second flow to form an enriched second flow and a depleted first flow, while concurrently maintaining a second component of the plurality of components in the first flow, the first component having a first sedimentation rate of the plurality of sedimentation rates and the second component having a second sedimentation rate of the plurality of sedimentation rates, wherein the first sedimentation rate is comparatively greater than the second sedimentation rate; differentially removing the enriched second flow from the depleted first flow; and holographically manipulating the second component in the depleted first flow.

The second exemplary method may also include additional separation stages, such as a holographic separation, including: providing a third flow; contacting the depleted first flow with the third flow to provide a second separation region; and holographically trapping the second component and moving the second component from the depleted first flow into the third flow while concurrently maintaining a third component of the plurality of components in the depleted first flow.

An exemplary apparatus embodiment of the invention for separating a fluid mixture into constituent, non-motile components includes: a first sorting channel having a first inlet for a first flow and a second inlet for a second flow; the first sorting channel further having a first outlet for the first flow and a second outlet for the second flow, the first sorting channel further having means to maintain the first flow and second flow substantially non-turbulent, the first sorting channel adapted to allow a first component in the first flow, of a plurality of components in the first flow, to sediment into the second flow to form an enriched second flow and a depleted first flow, while concurrently maintaining a second component of the plurality of components in the first flow; a second, optically transparent sorting channel having a first optical inlet coupled to the first outlet for the first flow and having a first optical outlet, the second, optically transparent sorting channel further having a second optical inlet for a third flow and a second optical outlet for the third flow; and a holographic optical trap coupled to the second, optically transparent sorting channel, the holographic optical trap adapted to generate a holographic optical trap to select and move the second component from the first flow into the third flow. The various components which are separated, for example, may be the various blood fractions or other biological materials, such as separations of motile from non-motile sperm.

Another apparatus or system for separating a plurality of components in a fluid comprises: an optically transparent sorting channel having a first inlet for a first flow and a second inlet for a second flow, the optically transparent sorting channel further having a first outlet for the first flow and a second outlet for the second flow; and a holographic optical trap system coupled to the optically transparent sorting channel, the holographic optical trap system adapted to generate a holographic optical trap to select and move a first component in the first flow, of a plurality of components in the first flow, into the second flow to form an enriched second flow and a depleted first flow, while a second component of the plurality of components is concurrently maintained in the first flow.

Another method embodiment provides for separating a plurality of cells, comprising: providing a first flow having the plurality of cells; providing a second flow; contacting the first flow with the second flow to provide a first separation region; and differentially sedimenting a first cell of the plurality of cells into the second flow while concurrently maintaining a second cell of the plurality of cells in the first flow. The method generally also includes differentially removing the second flow having the first cell from the first flow having the second cell. The method may also provide for providing a third flow; contacting the first flow with the third flow to provide a second separation region; and differentially sedimenting the second cell of the plurality of cells into the third flow while concurrently maintaining a third cell of the plurality of cells in the first flow. In addition, a plurality of second cells may be holographically separated from the first flow, and a plurality of contaminants or biological debris may be holographically removed from the first flow.

In another embodiment consistent with the present invention, optical trapping (or laser steering), which is a technology which has been used as a tool for manipulating microscopic objects, is used. An accepted description of the effect is that tightly focused light, such as light focused by a high numerical aperture microscope lens, has a steep intensity gradient. Optical traps use the gradient forces of a beam of light to trap a particles based on its dielectric constant To minimize its energy, a particle having a dielectric constant higher than the surrounding medium will move to the region of an optical trap where the electric field is the highest.

Optical trapping of the present invention is used to address cell sorting and purification (e.g., from contaminants such as viruses and bacteria) in several ways. For example, the forces exerted by optical traps on a material are sensitive to the exact distribution of the dielectric constant in that material—the optical force therefore depends on the composition and shape of the object.

Further, other forces on the object are sensitive to the hydrodynamic interaction between the object and the surrounding fluid—control of the fluid flow probes material shape, size and such features as surface rugosity.

Still further, localizing an object at a known position allows additional methods of automated interrogation such as high speed imaging and particle-specific scattering measurements.

In one embodiment consistent with the present invention, in achieving a multi-trap system, a diffractive optical element ("DOE", i.e., a phase shifting hologram utilizing either a transmission or a reflection geometry) is used to alter a single laser beam's wavefront. The wavefront is altered so that the downstream laser beam essentially becomes a large number of individual laser beams with relative positions and directions of travel fixed by the exact nature of the diffractive optical element.

The present invention provides optical trapping by focusing a laser beam with a lens to create an optical trap wherein the lens has a numerical aperture less than 0.9, and preferably decreases until it is most preferably less than 0.1.

Sorting using holographic laser steering involves establishing classes of identification for objects to be sorted, introducing an object to be sorted into a sorting area, and manipulating the object with a steered laser according to its identity class. The manipulation may be holding, moving, rotating, tagging or damaging the object in a way which differs based upon its identity class. Thus, the present invention provides a way of implementing a parallel approach to blood cell sorting and sperm cell sorting using holographic optical trapping.

In one embodiment of the present invention, spectroscopy of a sample of biological material may be accomplished with an imaging illumination source suitable for either inelastic spectroscopy or polarized light back scattering, the former being useful for assessing chemical identity, and the latter being suited for measuring dimensions of internal structures such as the nucleus size. Using such spectroscopic methods, in some embodiment, cells are interrogated. The spectrum of those cells which had positive results (i.e., those cells which reacted with or bonded with a label) may be obtained by using this imaging illumination.

A computer program may analyze the spectral data to identify the desired targets (i.e., cells bearing either an X or Y chromosome, or a suspected cancerous, pre-cancerous and/or non-cancerous cell types, etc.), then may apply the information to direct the phase patterning optical element (i.e., optical traps) to segregate or contain those desired or selected targets (i.e., cell types). The contained cells may be identified based on the reaction or binding of the contained cells with chemicals, or by using the natural fluorescence of the object, or the fluorescence of a substance associated with the object, as an identity tag or background tag. Upon completion of the assay, selection may be made, via computer and/or operator, of which cells to discard and which to collect.

Manipulation of cells in general, is made safer by having multiple beams available. Like a bed of nails, multiple tweezers ensure that less power is introduced at any particular spot in the cell. This eliminates hot spots and reduces the risk of damage. Any destructive two-photon processes benefit greatly since the absorption is proportional to the square of the laser power. Just adding a second tweezer decreases two-photon absorption in a particular spot by a factor of four. Trapping large cells involves a large amount of laser power for effective trapping. Putting the power into a single trap may cause immediate damage to the cell.

The manipulation of even just a single cell is greatly enhanced by utilizing holographic optical trapping, for example. A single cell may be manipulated by a line of tweezers, which lift the cell along the perimeter on one side. The resulting rotation allows a 360 degree view of the cell. In addition to the advantage for viewing of biological samples, there also exists the ability to orient samples stably, which has clear benefit for studies such as scattering experiments which have a strong dependence on orientation of the sample.

Sorting with a wide field of view has many advantages such as higher throughput. However, standard tweezing in a WFOV (wide field of view) may fail due to excessive radiation pressure. Tweezing with a wide field of view using holographic optical trapping may permit the ability to form exotic modes of light which greatly reduce the radiation pressure of the light beam. Vortex traps, for example, have a dark center because the varying phases of light cancel in the center of the trap. This dark center means most of the rays of light which travel down the center of the beam no longer exist. It is exactly these beams which harbor most of the radiation pressure of the light, so their removal greatly mitigates the difficulty in axial trapping. Other modes, e.g., donut modes, have the same advantage.

In one embodiment consistent with the present invention, the method and system lends itself to a semi-automated or automated process for tracking the movement and contents of each optical trap. In one embodiment consistent with the present invention, movement may be monitored via an optical data stream which can be viewed, or converted to a video signal, monitored, or analyzed by visual inspection of an operator, spectroscopically, and/or by video monitoring. The optical data stream may also be processed by a photodetector to monitor intensity, or any suitable device to convert the optical data stream to a digital data stream adapted for use by a computer and program. The computer program controls the selection of cells and the generation of optical traps.

In other embodiments consistent with the present invention, the movement of cells is tracked based on predetermined movement of each optical trap caused by encoding the phase patterning optical element. Additionally, in some embodiments, a computer program maintains a record of each cell contained in each optical trap.

There has thus been outlined, rather broadly, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect; before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, in which:

FIG. 4 schematically illustrates a holographic optical trapping system in accordance with one embodiment consistent with the present invention.

FIG. 5 is a schematic diagram of a holographic optical trapping system for sorting objects in accordance with one embodiment consistent with the present invention.

FIG. 24B is a plan view of a multi-layer laminar flow sorter in accordance with one embodiment consistent with the present invention.

DETAILED DESCRIPTION OF THE EXEMPLARY EMBODIMENTS

Figure 1:
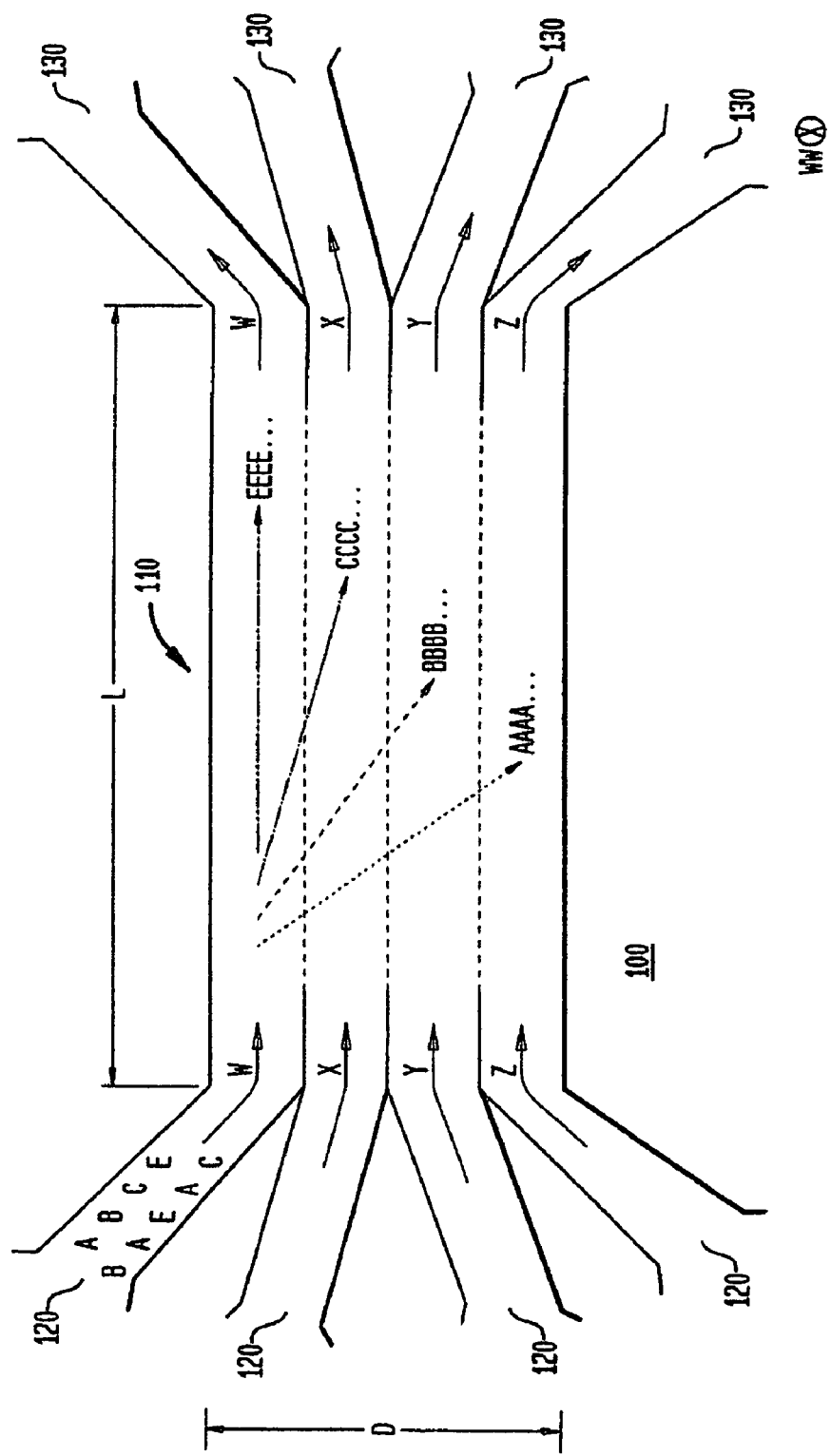
FIG. 1 is a lateral view of an apparatus 100 in accordance with one embodiment consistent with the present invention.

While the present invention is susceptible of embodiment in many different forms, there are shown in the drawings and will be described herein in detail specific embodiments thereof, with the understanding that the present disclosure is to be considered as an exemplification of the principles of the invention and is not intended to limit the invention to the specific embodiments illustrated.

As indicated above, the various embodiments of the present invention provide for separating components in a mixture, such as separating the various blood components of whole blood into corresponding fractions, such as a platelet fraction, a red blood cell fraction, a white blood cell fraction, and a plasma fraction. The various embodiments, as described below, utilize one or more sorting channels, having a plurality of substantially laminar flows, allowing one or more components to differentially sediment from one flow into another, thereby separating the components into corresponding flows. In addition, the various components may be sorted further using optical mechanisms, such as holographic optical trapping. The various embodiments of the present invention thereby provide separation of components on a continuous basis, such as within a continuous, closed system, without the potential damage and contamination of prior art methods, particularly for fractionation of blood components. The continuous process of the present invention also provides significant time savings for blood fractionation.

In addition to whole blood sorting and fractionation applications, the present invention is also suitable for other cell sorting applications, such as separations of cancer cells from normal or healthy cells in, for example, bone marrow extractions. The various embodiments of the present invention have further applicability to other biological or medical areas, such as for separations of cells, sperm, viruses, bacteria, cellular organelles or subparts, globular structures, colloidal suspensions, lipids and lipid globules, gels, immiscible particles, blastomeres, aggregations of cells, microorganisms, and other biological materials. For example, the component separation in accordance with the present invention may include cell "washing", in which contaminants (such as bacteria) are removed from cellular suspensions, which may be particularly useful in medical and food industry applications. Significantly, prior art flow-based techniques have not recognized any applicability to sorting or separation of non-motile cellular components using variable sedimentation rates and optical manipulation.

While discussion below focuses on the sorting of blood components to create different blood fractions, the apparatus, methods and systems of the present invention may be extended to other types of particulate, biological or cellular matter, which are capable of sedimenting or creaming within a fluid flow, or which are capable of being manipulated optically between different fluid flows. For example, the methodology of the present invention could be utilized to separate non-motile or non-viable sperm cells from viable cells, by allowing the non-motile cells to sediment from a first flow into a second flow while retaining the motile cells in the first flow or allowing the motile cells to move to a third flow. Other sorts of cell separation may also be performed, such as separating islet cells from other types of pancreatic cells, or otherwise separating islet cell clusters of different sizes, through either or both flow separation or optical tweezing (tapping). Viruses, proteins and other large molecules having different sedimentation rates may also be separated with the present invention. The holographic optical trapping utilized with the various separation stages may also be particularly useful in these other types of cell or particle separations.

The present invention has other medical applications as well. For example, the various laminar flows discussed below may be utilized as part of a kidney dialysis process, in which whole blood is cleansed of waste products and returned to the patient. As a consequence, in addition to particle separations based upon relative density, for example, the present invention may be utilized for separations based upon diffusion, motility, and other types of gradients.

For example, the present invention may be utilized to move a species from one solution to another solution where separation by filtering or centrifugation is not practical or desirable. In addition to the applications discussed above, additional applications include isolating colloids of a given size from colloids of other sizes (for research or commercial applications), and washing particles such as cells, egg cells, etc. (effectively replacing the medium in which they are contained and removing contaminants), or washing particles such as nanotubes from a solution of salts and surfactants with a different salt concentration or without surfactants, for example.

The action of separating species may rely on a number of physical properties of the objects including self-motility, self-diffusivity, free-fall velocity, or action under an external force, such as an electromagnetic field or a holographic optical trap. The properties which may be sorted upon include cell motility, cell viability, object size, object mass, object density, the tendency of particles to attract or repel one another or other objects in the flow, object charge, object surface chemistry, and the tendency of certain molecules to adhere to the object.

While the present invention is discussed in detail with respect to the apparatus 100, 200 and 300, it should be understood that this discussion applies equally to the various other embodiments illustrated in FIGS. 13-24 and 26-27.

FIG. 1 is an illustration of a lateral view of an apparatus 100 in accordance with the present invention. As illustrated in FIG. 1, the sorting apparatus 100 includes a sorting channel 110, a plurality of inlets 120 and a plurality of outlets 130. A corresponding fluid flow, such as illustrated flows W, X, Y and Z, enters one of the inlets 120 and flows, substantially non-turbulently or otherwise as a laminar flow, across the sorting channel (or sorting region) 110, and out through a corresponding outlet 130, as illustrated.

The apparatus 100 (and 200, below) may be constructed of a plurality of materials, integrally or as discrete components, using a wide variety of materials, such as metals, ceramics, glass, and plastics. Various materials and fabrication methods are discussed in the third and fourth related applications, and include, for example, use of various polymers which cure under UV exposure. Other details are also provided in the third and fourth related applications, such as the use and selection of different types of pumps, such as syringe pumping, peristaltic pumping, gravity-driven pumping, and various combinations of pumping actions.

In selected embodiments, when coupled with holographic trapping or other form of optical tweezing, the apparatus 100 (or 200) is transparent to the selected wavelength of the holographic generator, such as optically transparent when the holographic generator utilizes visible wavelengths. Depending upon the selected application, the apparatus 100 (200) should also be sterile and may also have a controlled temperature. The various fluid flows may be fed into the inlets 120 through a wide variety of means known to those of skill in the art and are within the scope of the present invention, including use of peristaltic pumps or a gravity feed, for example, and such means may also be utilized to control the flow rates of the various flows W, X, Y and Z. When peristaltic pumps are utilized, to maintain a constant flow rate and pressure, bubble-traps may be incorporated at the inlets 120 of the apparatus 100 (or 200).

The various fluids utilized in the separation flows may be diluted or concentrated, to increase or decrease the volume of one of the solutions, or to impact the concentration of some dissolved or suspended material, or to impact physical properties of the solution such as its viscosity, temperature, or density. Examples for the apparatus 100, when used for blood sorting, include: (a) dilution of the blood to reduce clogging or hydrodynamic interaction between blood cells, (b) extension of the volume of the blood or a blood fraction, (c) modification of the density of the blood, a blood fraction, or another solution which impacts the flow properties or separation behavior, (d) extension of the volume of a solution to maintain in increase fluid volume, especially in circumstances when fluid volume is being removed from the system. As discussed in greater detail below, various chemical attractants and repellants may be added to the fluids, which may also be at different temperatures and viscosity levels, to improve sperm sorting.

The various fluids utilized in the separation flows also may be "activated", such that some process is activated within the solution by some external influence or mixing with an external solution. Examples of external influences include: (a) applying an electric field, (b) applying a magnetic field, (c) exposing to light, (d) modifying the temperature, (e) introducing a chemical, (f) introducing a biological material, (g) shearing the solution, and (h) vibrating the solution. Examples of the activation which is caused by the external solution include: (a) alignment of particles, molecules, or cells, (b) polarization of one or more components of the solution, (c) cross-linking, (d) initiation or termination of chemical reaction, (e) initiation or termination of a biological response, (f) changing the type or rate of a chemical, physical, or biological response, or (g) causing a response or separation which depends upon the character of the particular component which is responding. Examples for the apparatus 100, when used for blood sorting, include: (a) addition of an agent to reduce clotting, (b) addition of agents to preserve viability or health of the blood solution or its components; (c) addition of agents which may augment the sorting process, such as by binding or collecting near certain components, thereby influencing one or more of their physical properties, including the addition of beads or other particles or polymers which may adhere to one or more species, and also including the introduction of salts or other materials which may influence the electrostatic interaction of materials or the hydrodynamic size or character of the materials; (d) addition of agents which may influence the flow properties, such as by changing the density, viscosity, surface tension, or other parameters; (e) addition of agents to enhance or suppress the aggregation of certain materials; and (f) addition of agents to enhance or suppress the adherence of certain materials to other materials or parts of the flow device.

In accordance with the invention, one of the fluid flows, such as the illustrated flow W, contains a plurality of components A, B, C and E. For example, when the fluid is whole blood, these components may be red blood cells ("RBC"), white blood cells ("WBC"), platelets, cellular debris and contaminants, all in plasma. Typically, many of the plurality of components have different sedimentation rates, typically measured using a Svedberg coefficient. For example, RBCs have a comparatively greater sedimentation rate than platelets, and will be expected to sediment faster on a passive basis, such as due to gravitational or buoyant forces, without the intervention of other, active mechanisms, such as centrifugation. As the various flows W, X, Y and Z flow through the sorting region 110, based upon different sedimentation rates, the plurality of components (such as cells or other particles) will sediment, moving from one flow to another. As illustrated, component A having the comparatively greatest sedimentation rate is illustrated as having moved from flow W to the lowest flow Z, component B having the comparatively next highest sedimentation rate is illustrated as having moved from flow W to the flow Y (above Z), component C having a comparatively smaller sedimentation rate is illustrated as having moved from flow W to the flow X (above Y), while component E having the comparatively smallest sedimentation rate, is illustrated as having remained in flow W (above Y). Using these different sedimentation properties, each of these components may be separated into a corresponding flow, and isolated from each other as each flow exits through its corresponding outlet 130. As each flow W, X, Y and Z exits through its corresponding outlet 130, that flow is differentially removed from the other flows, i.e., the flow is removed while the other flow remains intact or is otherwise separately removed from the remaining flows. In addition, this differential removal may be concurrent, namely, all flows removed concurrently or continuously.

Continuing to refer to FIG. 1, using whole blood with an anticoagulant (such as sodium citrate or heparin) as the fluid flow W, for example, the various blood fractions may be separated from each other, with red blood cells sedimenting fastest and represented by component A (e.g., 4.59 μm/s), white blood cells sedimenting at a slightly lower rate and represented by component B (e.g., 2.28 μm/s), platelets sedimenting at a comparatively slower rate and represented by component C (e.g., 0.055 μm/s), and plasma continuing to comprise flow W and represented by component E. Each blood fraction may then be removed through a corresponding outlet 130.

Not separately illustrated in FIG. 1, due to buoyant forces and relative density considerations, there may be particles or components in one or more of the fluid flows which will flow up to a higher flow (e.g., creaming). For example, less dense particles entering through flow X may rise into flow W, and exit with flow W through a corresponding outlet 130.

Illustrated in lateral view, the sorting channel (or sorting region) 110 of apparatus 11 has a varied length "L" parallel to the direction of flow, a depth "D" perpendicular to the direction of flow, and a width "WW", illustrated as extending into the page (and designated WW to avoid confusion with the W flow). These various dimensions may be selected based on a plurality of factors, particularly the flow rates and the sedimentation rates of the components of interest. For example, for a selected flow rate, the total length of the sorting channel should be long enough to differentially remove the component having the comparatively slowest sedimentation rate, illustrated as component C in FIG. 2, with shorter lengths corresponding to other flows for separation of components having faster sedimentation rates, as illustrated for flow Z having component A and flow Y having component B.

The present invention is further distinguished from the prior art by having considerably more latitude or tolerance for aspect ratios, while nonetheless maintaining a substantially laminar flow. The aspect ratio of length to width, for example, may vary from about 5 (or more) to 1 (5:1), with the length being greater than the width, to about 1 (or less) to 2 (the length being smaller than the width). A preferred length to width aspect ratio is about 2:1, and may vary from 3:1 to 1:2.

Flow rates may also vary between the plurality of flows utilized in apparatus 100. For example, higher flow rates in the lower level flows (such as Y and Z) may tend to compress the flows W and X, resulting in a shorter distance that certain components must traverse to sediment into the flows Y and Z.

In addition, the sedimentation of components through the various flows of the apparatus 100 is typically rate zonal, that is, based upon both relative density and size of the components to be separated, as well as the material's shape and electrostatic properties. Under other conditions, however, such as slower flow rates, thinner flow depths, and/or longer sorting channels 100, the sedimentation may also be isopycnic, that is, based only upon relative density of the components.

When isopycnic separation is desired, the various fluids comprising the flows W, X, Y and Z may be selected and adjusted to create desired density gradients to match the component densities for the selected separations. For example, the various fluids comprising the flows W, X, Y and Z may be selected and adjusted to each have a different, increasing or decreasing density, creating a stepped density gradient, with various particles sedimenting to the appropriate step. In addition, through use of a sufficient number of fluid flow layers, the density gradient will effectively become continuous, with a corresponding ability for fine-grained separation.

The various fluids comprising the generally laminar flows, such as flows W, X, Y and Z, may also be selected based on suitable criteria for the particular desired component separation. For example, for blood separation, the various flows may be comprised of whole blood, such as for flow W, and plasma or buffering solutions for the remaining flows. The various fluids may also be preprocessed prior to entry through the inlets 120, such as through dilution, addition of other components such as additives (such as anticoagulants, flocculants, or binding agents), viscosity or other flow property manipulation, or preprocessed through other separation techniques. Also for example, whole blood may be preprocessed to initially remove some red blood cells or to add an anticoagulant such as sodium citrate.

While illustrated with four flows or channels, it should be understood that the apparatus 100 (or 200, below) may be implemented with any number of flows and corresponding fluid inlets 120 and outlets 130. One limitation to the number of fluid flows is based on the ability to maintain each flow in a substantially laminar or non-turbulent manner, such that each interface between flows is substantially non-turbulent, to minimize any unwanted mixing of flows. In addition, there also may be relative density considerations for the fluids comprising the flows which could also result in limiting the number of flows utilized in a given stage of separation.

The various apparatus 100 (or 200, below) may be further coupled to additional apparatus 100 (200, below), in parallel for higher throughput, and in series for additional separation stages, such as for increased purity levels. In addition, the various apparatus 100 may also be combined with non-sedimentation separations, or be coupled in series with subsequent separations using non-sedimentation mechanisms, with additional separation of components between flows accomplished, for example, using optical forces such as holographic optical trapping of the fifth related application, incorporated herein by reference. These various apparatus 100, 200 or 300, moreover, may have different dimensions and different numbers of channels or flows.

Figure 2:
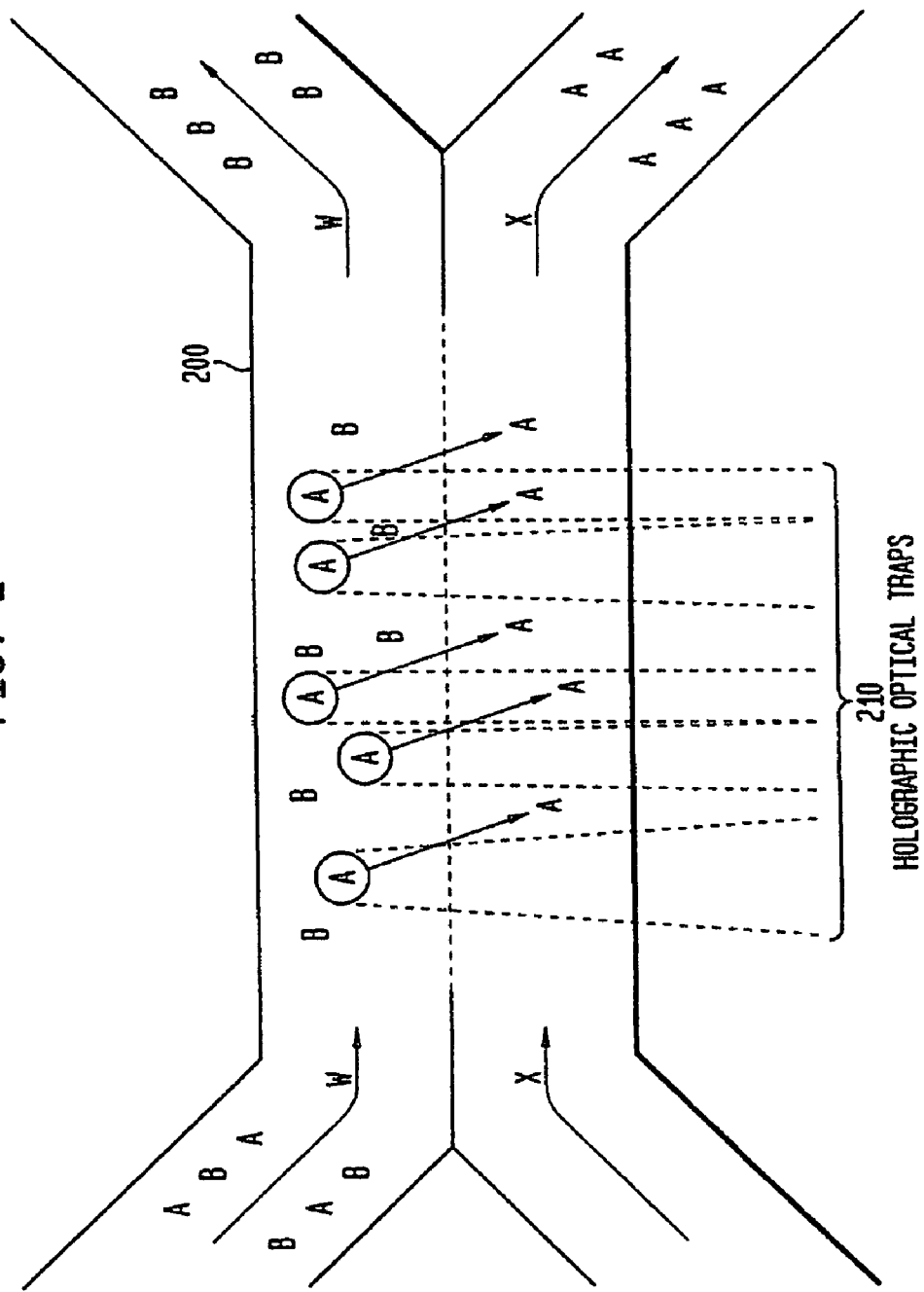
FIG. 2 is an illustration of optical trapping for component separation in an apparatus 200.

FIG. 2 (and also FIG. 13) is a general illustration of using such optical forces created by holographic or optical trapping for additional component separation in an apparatus 200. Creation and manipulation of the plurality of holographic optical traps 210 is explained in greater detail below with reference to FIGS. 4 and 5, with apparatus 200 forming the sample 506 of FIG. 5. Two flows W and X are illustrated in FIG. 2, with flow W initially having two components A and B. Holographic optical traps 210 (illustrated as conic sections in FIG. 2) are then utilized to capture "A" components, and move them into flow X. Such optical trapping is particularly useful for increased purification of a particular fraction, particularly for fractions having insufficient differentiation based on sedimentation rates. Such optical trapping is also particularly useful for removal of undesirable components, such as cellular debris and other impurities. In addition, where mixing or remixing of components may have occurred during the rate zonal laminar flow separations discussed above, the optical trapping may be particularly accurate in removing undesired components. For example, a comparatively small portion of white blood cells may not have sedimented fast enough, resulting in some white blood cell contamination of a platelet fraction. Optical trapping may be utilized to select and move the white blood cells into a separate flow, increasing the purity of the platelet fraction.

For blood sorting applications, it should be understood that platelets and RBC optically manipulate (or "tweeze") better than white blood cells. Using lower numerical apertures in the system 500 (discussed below), however, significantly improves optical manipulation of white blood cells.

When implemented in conjunction with optical traps, the apparatus 100, 200 or 300 should be embodied utilizing an optically transparent material, for the selected optical wavelength. When the holographic traps are implemented at other wavelengths, other correspondingly transparent materials may be utilized which are suitable for the selected wavelength. The apparatus 100, 200 or 300 is then implemented and placed in the location of the sample 506 illustrated in FIG. 5, with the system 500 utilized to perform the holographic optical trapping as one of or as part of a separation stage of the present invention.

Figure 3:
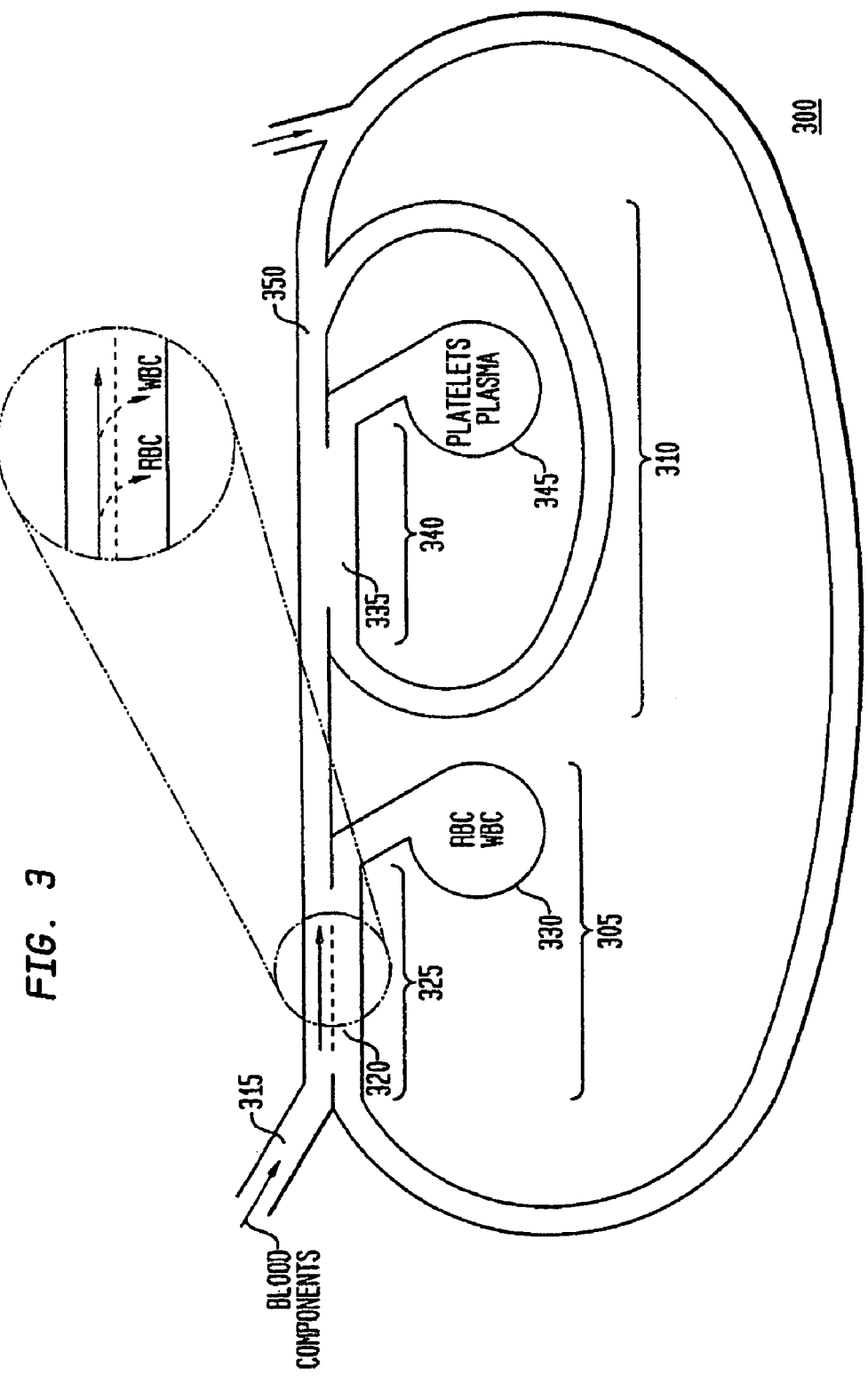
FIG. 3 is a diagram illustrating a closed, two-stage system 300 for blood component separation in accordance with one embodiment consistent with the present invention.

FIG. 3 is a diagram illustrating a closed, two-stage system 300 for blood or other component separation in accordance with the present invention. In a first stage 305, blood components from a selected donor flow through inlet 315 to form a first flow, and plasma is returned (or primed on initial start up) through inlet 320 to form a second flow. The first and second flows are non-turbulent and otherwise laminar flows, and make non-turbulent contact with each other in first separation region 325, forming a non-turbulent interface region between the two flows. In the first separation region 325, both red blood cells and white blood cells sediment from the first flow into the second flow, and are collected in reservoir 330 for other uses (such as medical uses for packed cells) or for return to the selected donor. As indicated above, both the length of the first separation region 325 and the flow rate of the first flow are predetermined such that both red blood cells and white blood cells have sufficient time to passively sediment into the second flow, under gravitational and buoyant forces.

Continuing to refer to FIG. 3, the first flow, now substantially depleted of both red blood cells and white blood cells, flows non-turbulently on a continuous path into a second separation stage 310. In the second separation stage 310, the first flow enters a second separation region 340 with a third flow from inlet 335. The third flow is also comprised of plasma from the selected donor in the exemplary embodiment. In the second separation region 340, the platelets remaining in flow one passively sediment into flow three, and are collected with the plasma of flow three in reservoir 345 for medical use, for example. The further depleted flow one is then recirculated from outlet 350 back to inlets 320 and 335, to form the first and third flows, respectively. As indicated above, the system 300 may be primed with donor plasma at system start-up by, for example, centrifuging a portion of the selected donor's blood, or by initially using another biocompatible, non-toxic liquid until a depleted flow one (substantially or predominantly plasma) is generated at outlet 350.

Not separately illustrated in FIG. 3, an additional holographic trapping separation stage may also be utilized to aid in the separation of these blood fractions. For example, a holographic trapping separation stage may be utilized in lieu of or in addition to, second stage 310. In addition, while the second stage separation has been illustrated using flow one, in other embodiments, flow two may be subjected to a second (or more) stage separation, in addition to or in lieu of the additional separation stage of flow one. Moreover, additional separation stages may be utilized in series or in parallel.

More generally, separation regions are regions where materials are partially or fully sorted or separated based upon some material property. The separation regions may employ one or more of the following techniques, individually, serially, or simultaneously, in any of the various flows in the embodiments of the invention:

(a) Sedimentation Rate Zonal Separation: separation by sedimentation rate. The sedimentation rate is generally a function of the material's size and density, as well as the material's shape and electrostatic properties. For this separation, laminar flow is set up and separation occurs under gravity, or in some cases through other inertial forces such as spinning in a centrifuge-like device.

(b) Isopycnic Separation: separation by density. For this separation, a linear, step, smoothed-step, or alternate density gradient is established and the materials are allowed to sediment and/or cream in the gradient until the material reaches or nearly reaches an area where the material is in an environment of matched density.

(c) Diffusivity Separation: separation by diffusivity. For this separation, materials are fractionated based upon the distance they diffuse in a given amount of time.

(d) Motility Separation: separation by motility. In this separation, materials are fractionated based on the distance the material travels under its own motility in a given amount of time.

(e) Optical Fractionation: separation using optical forces, typically without feedback mechanisms to inform and influence the optical system based upon investigation of the individual objects.

(f) Direct Optical Separation: separation using optical forces, typically using feedback mechanisms to inform and influence the optical system based upon investigation of the individual objects.

(g) Dielectrophoretic Separation: separation using dielectrophoresis. The forces exerted upon an object depends upon its position in the imposed electric field and the dielectric response of the material and its environment.

(h) Electrophoretic Separation: separation using electrophoresis. The forces exerted upon an object depends upon its position in the imposed electric field and the charge of the material and its environment.

(i) Magnetic Separation: separation using magnetic forces. The forces exerted upon an object depends upon its position in the imposed magnetic field and the magnetic properties of the object.

(j) Surface Tension Separation: separation using the surface tension or surface chemistry of a material. This may, for example, involve the creating of fluid interfaces which certain materials may be attracted to or stable at.

More particularly, exemplary separations for blood sorting include: (a) separation of one or more blood cell types from some or all of the other blood cell types and/or from the blood plasma or fluid medium by sedimentation rate zonal separation; (b) separation as in (a) but with isopycnic separation; (c) removal of just the red blood cells (RBCs) or the RBCs and white blood cells (WBCs) from the solution by sedimentation; (d) concentration of the platelets from the plasma using sedimentation; (e) extraction of the RBCs using dielectrophoresis, electrophoresis, or magnetic separation; (f) concentration or extraction of platelets from a solution using optical techniques including optical tweezers and optical fractionation; and (g) separation of blood components using agents which may bind to a particular cell type (such as functionalized beads) and be acted upon by any of the above separation techniques, after which the agent may or may not be unbound from the cell type.

For blood sorting, a combined approach may be the most effective, such as: first extract most of the RBCS and WBCs using sedimentation rate zonal separation, then extraction and concentration of the platelets using optical fractionation, discussed below. The optical fractionation step will act not only to concentrate the platelets (which could also, for example, be done by a centrifugation step at the end), but will provide a second step which will exert strong suppression on the WBCs accidentally collected with the platelets, for the example of platelet aphoresis. Such concentration steps may also include filtering, such as to filter WBC from a platelet fraction or a plasma fraction.

While apparatus 300 has been described with respect to blood fractionation, it will be understood by those of skill in the art that the apparatus 300 may be utilized for a wide variety of separations, in addition to such blood fractionation. In addition, apparatus 300 may also be considered one particular embodiment of series-connected separation stages of the present invention.

Cell "washing" is also a significant application of the apparatus 100, 200 or 300. Such washing may include a change of media, for storage, preservation, or other medical purposes. Such washing may also consist of removing a media containing contaminants such as bacteria, by separating the cells of interest into another media flow free of such contamination. As indicated above, sperm separation is also a significant application of the apparatus 100, 200 or 300.

Portions of, or outputs from, the sorting device 100, 200 or 300 may be inspected optically. This may be direct visual imaging, such as with a camera, utilizing direct bright-light imaging or fluorescent imaging. Or, it may be more sophisticated techniques such as spectroscopy, transmission spectroscopy, spectral imaging, or scattering such as dynamic light scattering or diffusive wave spectroscopy. In many cases, these inspection regions may be incorporated directly into the flow device to characterize the inputs, outputs, or intermediate steps. They may be for diagnostics or record-keeping, or they may be used to inform the overall process, such as for feedback on how processing is done or on the speed of flow or amount of each solution to use. In some cases, the optical inspection regions may be used in conjunction with additives, such as chemicals which bind to or affect parts of the solution or beads which are functionalized to bind and/or fluoresce in the presence of certain materials or diseases. For the example of blood sorting, these techniques may be used to measure cell concentrations, to detect disease, or to detect other parameters which characterize the blood.

Portions of, or outputs from, the sorting device 100, 200 or 300 also may be characterized electronically. For example, a portion of the sorting device may have electronic devices embedded. Example electronic devices may include: (a) capacitors, (b) electronic flow meters, (c) resistance meters for determining the bulk conductivity of the fluid, from which concentrations or compositions may be measured, or (d) pH measuring devices. For the application of blood sorting, measurements of cell concentration, iron content, flow rates, total cell counts, electrolyte concentration, pH, and other parameters may be a valuable part of a sorting device.

The flow components of the sorting device 100, 200 or 300 may be passive, being completely controlled externally by the flow rates of the inputs and outputs. Alternatively, there may be active flow components embedded in the device (not separately illustrated), such as valves which may be partially or fully opened or closed using electronic, optical, thermal, mechanical, or other influence. For the application of blood sorting, the sorting device 100, 200 or 300 may have an integrated method for storing and/or delivering one or more solutions. For example, a consumable sorting device may be manufactured to have a deformable membrane on a side of a reservoir. This reservoir may be filled with a solution, such as a buffering agent which is biologically compatible with the patient and which may be used to dilute the blood. Another example is that it could be filled with an anti-coagulant. The delivery and/or use of one such fluid may be actively controlled by mechanical influence, pressing on the membrane to deliver the fluid. Alternately, another mechanism may be used to deliver the fluid. Of particular interest, for the sake of simplicity and cost-saving, is the integration of various fluid solutions needed at differing steps in the sorting. Integrating these components may result in substantial simplification and reduction of the total cost of ownership and operation. It may also reduce the risk of contamination and error. Such reservoirs holding input and buffering solutions or fluids are illustrated, for example, in FIGS. 14 and 15.

The device 100, 200 or 300 may include areas (not separately illustrated) where biological or chemical investigation of one or more of the fluids or fluid components. This may include measurements of pH, the presence of certain biological or chemical materials, or other measurements. For the application of blood sorting, this may include detection of disease, characterization of concentrations of various cell types or materials in the plasma, characterization of iron content, determination of blood type, or other evaluation of blood quality, type, or category.

The device 100, 200 or 300 may include a region (not separately illustrated) which sterilizes the solution using optical methods, such as exposure to UV light, or other methods. The sterilization may act upon solutions which are initially part of the device or added to it for buffering, washing, diluting, or other impacts on the sample solution. Or, the sterilization may act upon part or all of the sample solution being processed. For the application of blood sorting, optical sterilization of the solutions used in the device other than whole blood may be important. Also, sterilization of the blood or certain fractions of the blood may be important.

The device 100, 200 or 300 may be comprised of materials such that one or more surfaces have been constructed so as to interact physically or chemically with certain materials. For example, a surface may be functionalized so that certain materials adhere to it, for the purpose of extracting these materials from the solution or for the purpose of diagnostics. For the application of blood sorting, functionalized surfaces may be used to extract unwanted materials from certain fractions. Alternately, they may be used to collect materials which are at low concentration for the purpose of measuring the degree to which a material or a type of material is present, such as for disease detection.

The sorting device 100, 200 or 300 may contain regions where sorting acts in parallel but without physical walls to separate the flows. For example, a parallel sorting region may have multiple inlets 120 and outlets 130, some of which are functionally similar to each other. Instead of having physical dividers distinguishing the multiple parallel sorters, the division occurs as a consequence of the physical properties of the solutions and the flow. The contacting parallelized sorters regions may yield high sorting rates with more simple and cheap devices. They may also act to avoid contact with surfaces. For blood sorting, these regions would be used to minimize contact with surfaces and to maximize sorting rate while reducing costs and complexity.

The device 100, 200 or 300 may have regions which are designed to regulate flow rate or the flow character (not separately illustrated). For example, in many cases laminar flow is required, and often a particular flow profile is desired. In other cases, several regions of the device should have identical flow rates and behavior. For these reasons, areas with shapes and other properties to influence flow behavior are often needed.

In some cases, this is done by making very symmetric flow designs. In other cases, large changes in the diameter of flow regions and/or the existence of reservoirs help to maintain uniform flow rates. In other cases, very carefully designed channels provide the exact balancing of flow rates needed. To maintain laminar flow, areas where slow changes in channel size occur may be important. Obstacles or dividers may also act to maintain laminar flow. For blood sorting, flow regulation is important to achieve high sorting rates while maintaining the yield and purity of the fractions.

Not separately illustrated, the device 100, 200 or 300 may contain regions which are designed for mechanical mixing of the fluids, such as regions which encourage turbulence. For example, a region with a fast narrow stream entering a region with a large dimension may produce turbulent flow and mixing. For blood sorting, a mixing region may mix a diluent or anticoagulant with the blood, or may mix other solutions together as needed.

The device 100, 200 or 300 may contain regions which align cells or materials in a certain way (not separately illustrated). This is sometimes done through shear flows, but may also be done by imposing external fields such as electric fields.

The device 100, 200 or 300 may contain regions designed to lyse cells or break up materials (not separately illustrated). This may be done through shear flows, vibration, forcing through an orifice, electrical, or other means. For blood sorting, this may be valuable for the elimination of certain cell types or aggregates which may form. It may also be valuable for diagnostic purposes, such as disease detection or measurement of parameters which pertain to the contents of cells.

The device may contain regions (not separately illustrated) which swell or dehydrate cells or objects, such as by introducing agents which change the osmotic pressure or by changing the physical pressure. This may be done, for example, as a step prior to isopycnic sorting to adjust the density of the cells or objects. It may also be done to kill or shock certain components. For the example of blood sorting, this may be done as a later stage purification step to remove or neutralize undesired components.

The device 100, 200 or 300 may contain regions which heat or cool one or more solutions (not separately illustrated). This may be done for its impact on physical properties, such as viscosity or density. Or, it may be done for its impact on chemical properties, such as chemical reaction rates or chemical stability. Or, it may be done for its impact on biological properties, such as motility, metabolism rate, or viability. For example, one fluid flow may be at a higher temperature than another, causing motile sperm to move away from the hotter fluid to the cooler fluid. Also, it may be done for system-level compatibility, such as in preparation for the following processing step. For the example of blood sorting; solutions which are returned to the patient may be maintained at an appropriate temperature to avoid chilling the patient. Solutions which are to be stored may be cooled during processing to preserve those fractions or prepare them for the next processing or storage step.

The device 100, 200 or 300 may contain reservoirs which serve to store solutions which will be used during the process run, or which may be generated during the process run (not separately illustrated). Having these reservoirs integral to the sorting device simplifies the use of the device and reduces the need for additional parts. For the example of blood sorting, reservoirs may contain anticoagulants, diluents, dilutants, and any other solutions needed in the process. Reservoirs may also be incorporated which will hold the sorted fractions or waste fractions.

The device 100, 200 or 300 may contain regions which enhance mixing by diffusion (not separately illustrated). For example, when mixing by contacting two laminar flows, parallelizing into many narrow contacting flows enhances the overall mixing rate by diffusion. For the example of blood sorting, diffusive mixing regions may be used to mix diluent, anticoagulant, or other solutions with whole blood or blood fractions.

Also not separately illustrated, the device may contain regions with bubble traps to remove air bubbles from the system. This may be done by having a region where air bubbles are able to rise from a region with flow to a region above the primary flow region. For the example of blood sorting, this may be done in a simple way to guarantee that small air bubbles from the loading or running of the system do not pass on to the patient or the collection samples.

As indicated above, the device 100, 200 or 300 may contain regions which act to suppress any pulsation in the flow (not separately illustrated), such as that which, occurs when peristaltic pumps are used. One way to suppress pulsation is to incorporate a "bubble-trap" into the device. The presence of an air pocket, which is in contact with the fluid, allows for compression of the air pocket as pressure in the fluid increases and decreases. Thus, the air pocket acts as a shock absorber, smoothing out the flow. Other devices may be used as well, such as a flexible membrane which may bend under higher pressures, thereby smoothing out the pressure and flow rate. For the application of blood sorting, pulsation reduction regions will yield more precise and smooth flows, and therefore higher sorting rates, purity, and yield.

The device 100, 200 or 300 may contain regions which reveal the state of the device (not separately illustrated). For a consumable, it may indicate whether the device has been sterilized or whether it has been used. For the application of blood sorting, one would want indicators to confirm both that the sorting device has been sterilized and that the device has not yet been used or contaminated.

The sorting device 100, 200 or 300, or overall sorting system, may contain mechanisms for precise leveling of the flow sorter. This is important because for some sorters, buoyant forces may cause unintentional flows and have negative impacts on sorting yields and purity in cases where the device is not precisely leveled. Additionally, the sorting device may contain components which reveal whether it is well-balanced, or the degree to which it is balanced. For example, it may have an electronic or gravity-based balance incorporated in the sorting device itself. One example of such a device is a shaped channel with fluid and an air bubble in it. The position of the air bubble may reveal the angle of the tilt of the device. Another such device may use a metal ball in a track to reveal the tilt angle. Another manifestation is to use an optical alignment, such as bouncing a light source off a surface or passing a light source through a wedge to identify its orientation. For the application of blood sorting, leveling controls and indicators are significant to guarantee high-yield and high-purity products.

The sorting device 100, 200 or 300, or overall sorting system, may contain mechanisms for maintaining uniform and/or constant temperatures of the device and/or the solution (not separately illustrated). This is important to eliminate thermally-induced buoyant forces which may cause unintentional flows and have negative impacts on sorting yields and purity. Additionally, the sorting device may have indicators in it, or in the sorting system as a whole, which indicate the temperature and/or temperature uniformity of one or more components. For the application of blood sorting, temperature uniformity controls and indicators may be significant to guarantee high-yield and high-purity products.

The sorting device 100, 200 or 300, or overall sorting system, may contain mechanisms for measuring the level and concentration of one or more input or output solution (not separately illustrated). These measurements may be used to gauge the speed of operation, completion time, error state, for general monitoring, or for other applications. For the application of blood sorting, level and concentration indicators may be used to identify when sufficient sample has been collected or to detect when a failure or depletion of a solution has occurred.

Lastly, the sorting device 100, 200 or 300, or overall sorting system, may, have a method for priming the system with one or more fluids using standard bottom-up filling or evacuation. Purging may similarly be done by draining the device or by flowing a solution through it. At the early stages of a sorting run, the priming solution may be discarded until a time when the priming solution has been mostly exhausted and the desired solution is obtained. Similarly, at the late stages of a sorting run, a fluid may be used to push the sorted material through the system to minimize waste and maximize yield.

Figure 26:
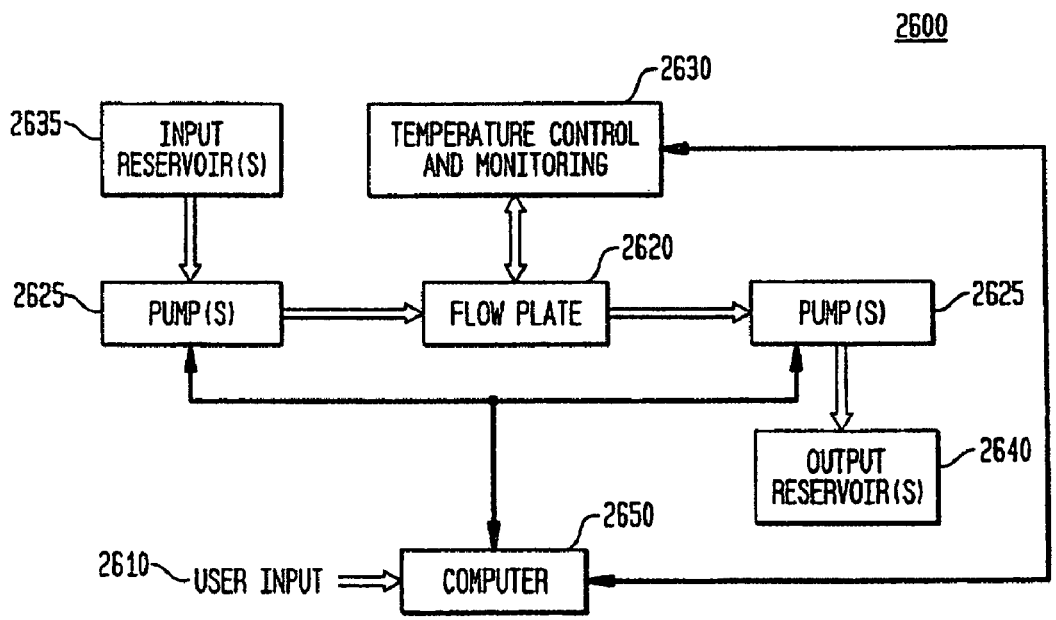
FIG. 26 is a block diagram illustrating an exemplary sorting and separation system in accordance with one embodiment consistent with the present invention.

The various sorting devices 100, 200 or 300 may also be utilized in a system providing a general purpose device which allows a user to extract one or more fractions of a solution, determined by a range of S values (size, density, or size*density). FIG. 26 is a block diagram illustrating an exemplary sorting and separation system 2600 in accordance with one embodiment consistent with the present invention. This general purpose sorter would vary the flow rates on each input and output channel in response to user controls (user input 2610). The user controls would allow the user to determine the range of S values that leave through each output channel. This device would be a valuable lab tool for performing various purifications, washing, separations, and diagnostic evaluations of samples. It would also be an important platform for research, development, and prototyping applications.

The sorting hardware may be contained within a single enclosure which may or may not be temperature controlled. This hardware consists of (1) Consumable flow plate 2620 (e.g., sorting device 100, 200 or 300) with several inputs and outputs, (2) several computer-controllable peristaltic pumps 2625, (3) temperature control and monitoring apparatus 2630, (4) reservoir holders (or reservoirs 2635 and 2640). The sorting is controlled by a computer 2650 which monitors and controls the flow rates, temperature, and any other additional components which may be included for controlling or diagnostics purposes.

The flow plate 2620 may be a simple general-purpose device, suitable for many applications, as discussed above. It may have two to four inputs and two to ten outputs. It may be provided in a sterile, primed, and sealed state. The reservoirs may be part of the flow plate, or they may be separate sterile components which are attached to the flow plate before use. All or a portion of the central sorting region may be covered with a cover glass to allow manipulation with optical tweezers, optical dielectrophoresis, or laser killing/cutting of samples.

The computer 2650 control does measurements and control of the hardware for pumping and temperature control. It may also interface other hardware components that may be added. The user software provides a very convenient front end to the simultaneous control of all the pumps. It would do the necessary math to control each pump rate to give the user the desired flows for the particular sorting application.

This system 2600 would be general enough to allow for many sorting applications, either independently or in conjunction with an additional laser apparatus. These applications include bin is not limited to: cell identification by fluorescence, cell killing by high intensity laser exposure, cell fractionation using optical dielectrophoresis, motile cell fractionation based on motility, passive sorting of objects by diffusivity, and passive fluidic zonal density sorting. The passive fluidic zonal density sorting applications, which are numerous and extend over a broad range, can generally be done with minimal or no additional hardware.

Exemplary uses and applications for such a general purpose sorting system 2600, using passive fluidic sorting and/or use of optical gradient forces (discussed below) are outlined in the following table:

| Category | General | Specific |
|---|---|---|
| Washing - Removing Components | Cell Washing for Disease Removal | Removing debris, bacteria, and viruses from human sperm<br>Removing debris, bacteria, and viruses from animal sperm |
| | Aggregate Removal | Removing undesirable clumps of materials in industrial processes<br>Removing aggregated colloids in solution<br>Removing coarsened droplets in an emulsion |
| | Precursor Removal | Removing precursor materials from a halted growth process<br>Separating differentiated cells<br>Removing blastocytes from incubating sperms and eggs |
| Washing - Changing Media | Cell Processing | Changing osmotic conditions - Cell swelling or shrinking<br>Cell staining<br>Automated multi-step cell experiments or processing<br>Sperm fluoridation to suppress activity |
| | Material Processing Assays | Bead dying<br>Object-solution response assays |
| Diagnostics | Characterizing Monodisperse Solutions | Measuring S (Svedberg coefficient) of particles<br>Measuring size of particles of known material<br>Measuring density of particles of known size<br>Measuring composition of particles |
| | Characterizing Polydisperse Solutions | Measuring distribution of S, size, density, composition, etc.<br>Measuring average S, size, density, composition, etc. |
| | Disease Detection | Extracting a sample of bacteria from infected tissue<br>Extracting a sample of bacteria from stool samples<br>Extracting a sample of bacteria from blood<br>Extracting cells that are infected with viruses from healthy cells |

| Category | General | Specific |
|---|---|---|
| | Environmental | Extracting spores from sample to determine spore count in air |
| | | Extracting particulate matter from water or air for environmental monitoring |
| | | Monitoring water safety in drinking or swimming water |
| | | Extracting spres from environmental samples to quantify mold levels in infected homes |
| | Food Safety | Extracting a sample of bacteria from food for diagnosis |
| Purifying - Reducing Variance | Viruses | Purifying a virus sample |
| Purifying - Extracting Components | Cell Components | Separating different cell components from solution of lysed cells |
| | Cell Components | Separating organelles |
| | Bacteria | Extracting a sample of bacteria from infected tissue |
| | Spores | Extracting a sample of spores from a solution |
| Filtering | Filtering Large Components From Foods | Removing yeast from beer |
| | | Removing yeast from wine |
| | | Removing fat from milk |
| | Industrial Filtering | Removing particulates from water |
| | | Removing particulates from machine oil |
| | Pharmaceutical Filtering | Removing undissolved clumps from solution to prevent overdosing |
| | Medical Filtering | Dialysis, using a membrane, for kidney dialysis |
| Sorting | Cell Type Sorting | Sorting blood cells from blood to extract the plasma |
| | | Sorting platelet cells from blood for aphoresis |
| | | Sorting cells based on presence of given antibody (may use functionalized beads) |
| | | Sorting natural killer cells from blood as a treatment for AIDS |
| | | Sorting different types of cells within a tissue or organ (eg. sorting osteoclasts, osteoplasts, osteoblasts) |
| | | Sorting white blood cells as a treatment for white blood cell diseases (e.g., high WBC such as leukemia or lymphomia, or low WBC) |
| | | Sorting sickle cells from normal red blood cells as a treatment for sickle-cell anemia |
| | Cell Cluster Sorting | Sorting islet cell clusters by size (diabetes) |
| | | Removing cell clusters from single cells |
| | Cell State Sorting | Removing infected cells from healthy cells |
| | | Removing living cells from dead cells |
| | | Separating proliferating and non-proliferating cells |
| | | Isolating viable sperm from inviable sperm |
| | Isolating Cells From Biopsies | Purifying bone marrow cells from blood in marrow biopsy |
| | Colloids Fractionation | Sorting colloids by size, density, composition, S, etc. |
| | Sorting Variants of One Cell Type | Sorting multizygotic sperm from normal sperm |
| | | Removing most severe RBCs in sickle cell anemia patients |

Figure 27:
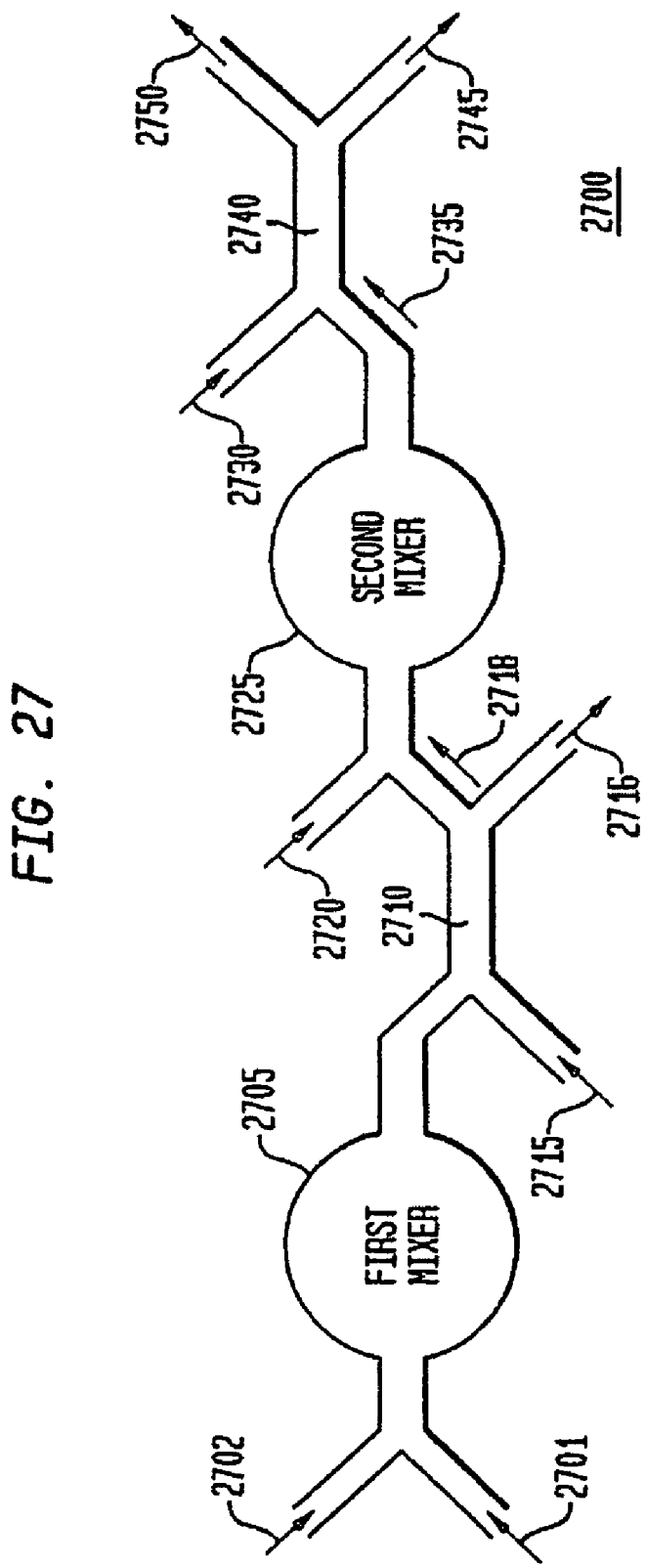
FIG. 27 is a block diagram illustrating an exemplary bioreactor product purification and separation system in accordance with one embodiment consistent with the present invention.

FIG. 27 is a block diagram illustrating an exemplary bioreactor product purification and separation system 2700 in accordance with one embodiment consistent with the present invention. A bioreactor is used in the production of monoclonal antibodies, recombinant protein products, viruses and viral antigens, and viable cell mass. The most common use for a bioreactor is in the production of various drug therapies. A bioreactor basically works by allowing cells to grow in high concentrations in ideal conditions. While the cells are growing a culture medium is flowed through the bioreactor. This medium collects the cell's waste products, as well as provides nutrition for the cells. The medium that has been flowed through the bioreactor is then processed for the product. In order to collect the product, the waste filled medium is filtered through many different processes, one of which is through bead column chromatography. This process takes a long time to complete, is very expensive, and does not yield a large percentage of the final product. The present invention solves all three of these problems.

The bioreactor product purifier 2700 would quickly, easily, and accurately remove the wanted product from the waste medium. The waste media would be flowed into the sorter through one channel 2701. At the same time a solution of beads coated with the proper affinity sites would be flowed into the sorter through the second channel 2702. Both channels would lead to a first mixer 2705 in which they would be mixed together. During the mixing the product would bind to the sites on the beads. The mixture would then flow through a first separation region 2710 along with an input buffer (input channel 2715). Through the use of passive diffusive sorting, the beads with selected product output through channel 2718 and the waste solution would be output through channel 2716 and discarded. Passive diffusive sorting succeeds because the large beads stay in one channel while the lighter molecules diffuse to the other side of the channel. The bead solution is then be flowed through channel 2718 as a denaturing solution is flowed through a second channel 2720. Both of these channels would flow to a second mixer 2725 where they would be mixed together. While they were being mixed, the denaturing solution would break the bond between the product and the beads. After mixing, the solution would be flowed through an output channel 2735 along with another buffer solution through channel 2730, into second separation region 2740. Through the use of passive diffusive sorting, the beads would be flowed through the bottom channel 2745 and be discarded as waste. The purified and recovered product would be flowed through the top channel 2750. This method of purification should reduce costs, reduce time, and increase the yield of final product.

FIG. 4 schematically illustrates a holographic optical trapping system 400, generally used in conjunction with an apparatus 100, 200 or 300, according to one embodiment consistent with the present invention. Additional detail concerning holographic optical trapping is available in the fifth related application. In a holographic optical trapping apparatus or system 400 as illustrated in FIG. 4, light is incident from a laser system, and enters as shown by the downward arrow, to power the system 400.

A phase patterning optical element 401 is preferably a dynamic optical element (DOE), with a dynamic surface, which is also a phase-only spatial light modulator (SLM) such as the "PAL-SLM series X7665," manufactured by Hamamatsu of Japan, the "SLM 512SA7" or the "SLM 512SA15" both manufactured by Boulder Nonlinear Systems of Lafayette, Colo. These dynamic phase patterned optical elements 401 are computer-controlled to generate beamlets by a hologram encoded in the medium which may be varied to generate the beamlets and select the form of the beamlets. A phase pattern 402 generated on the lower left of FIG. 4 produces the traps 403 shown in the lower right filled with 1 μm diameter silica spheres 404 suspended in water 405. Thus, the system 400 is controlled by the dynamic hologram shown below on the left.

The laser beam travels through lenses 406, 407, to dichroic mirror 408. The beam splitter 408 is constructed of a dichroic mirror, a photonic band gap mirror, omni directional mirror, or other similar device. The beam splitter 408 selectively reflects the wavelength of light used to form the optical traps 403 and transmits other wavelengths. The portion of light reflected from the area of the beam splitter 408 is then passed through an area of an encoded phase patterning optical element disposed substantially in a plane conjugate to a planar back aperture of a focusing (objective) lens 409.

In single beam optical trapping (also called laser or optical tweezers) it had been thought, prior to the invention of the fifth related application, that a high numerical aperture lens was necessary for acceptable optical traps. A basis for this thinking was that, for optical trapping, one uses the gradient in the electric field of the impinging light to trap the particle. In order to have a large trapping force it has been thought necessary to have a large gradient in the electric field (or number density of rays). The way that one usually accomplishes this is to pass the light field through a high numerical aperture lens.

A concern with observation and trapping of samples within a large field of view is that such observation and trapping would involve an objective lens with a low numerical aperture. Contrary to prior teaching, the invention of the fifth related application provides a low numerical aperture lens as, for example, the objective lens 409 in FIG. 4. The ability to observe and trap in this situation could be useful in any application where one would benefit from a large field of view given by a low magnification lens, such as placing microscopic manufactured parts or working with large numbers of objects, such as cells, for example.

As an example according to the present invention, 3 micron silica spheres 104 suspended in water 105 were trapped with lenses 109 with an unprecedented low numerical aperture. The lenses 109 used were manufactured by Nikon: (a) Plan 4× with an NA of 0.10; and (b) Plan 10× with an NA of 025.

Suitable phase patterning optical elements are characterized as transmissive or reflective depending on how they direct the focused beam of light or other source of energy. Transmissive diffractive optical elements transmit the beam of light or other source of energy, while reflective diffractive optical elements reflect the beam.

The phase patterning optical element 401 may also be categorized as having a static or a dynamic surface. Examples of suitable static phase patterning optical elements include those with one or more fixed surface regions, such as gratings, including diffraction gratings, reflective gratings, and transmissive gratings, holograms, including polychromatic holograms, stencils, light shaping holographic filters, polychromatic holograms, lenses, mirrors, prisms, waveplates and the like. The static, transmissive phase patterning optical element is characterized by a fixed surface.

In some embodiments, however, the phase patterning optical element 401 itself is movable, thereby allowing for the selection of one more of the fixed surface regions by moving the phase patterning optical element 401 relative to the laser beam to select the appropriate region.

The static phase patterning optical element may be attached to a spindle and rotated with a controlled electric motor (not shown). The static phase patterning optical element has a fixed surface and discrete regions. In other embodiments of static phase patterning optical elements, either transmissive or reflective, the fixed surface has a non-homogeneous surface containing substantially continuously varying regions, or a combination of discrete regions, and substantially continuously varying regions.

Examples of suitable dynamic phase patterning optical elements having a time dependent aspect to their function include computer-generated diffractive patterns, phase-shifting materials, liquid crystal phase-shifting arrays, micro-mirror arrays, including piston mode micro-mirror arrays, spatial light modulators, electro-optic deflectors, acousto-optic modulators, deformable mirrors, reflective MEMS arrays and the like. With a dynamic phase patterning optical element 401, the medium 405 which comprises the phase patterning optical element 401 encodes a hologram which may be altered, to impart a patterned phase shift to the focused beam of light which results in a corresponding change in the phase profile of the focused beam of light, such as diffraction, or convergence. Additionally, the medium 405 may be altered to produce a change in the location of the optical traps 403. It is an advantage of dynamic phase patterning optical elements 401, that the medium 405 may be altered to independently move each optical trap 403.

In those embodiments in which the phase profile of the beamlets is less intense at the periphery and more intense at regions inward from the periphery, overfilling the back aperture by less than about 15 percent is useful to form optical traps with greater intensity at the periphery, than optical traps formed without overfilling the back aperture.

In some embodiments, the form of an optical trap may be changed from its original form to that of a point optical trap, an optical vortex, Bessel beam, an optical bottle, an optical rotator or a light cage The optical trap may be moved in two or three dimensions. The phase patterning optical element is also useful to impart a particular topological mode to the laser light, for example, by converting a Gaussian into a Gauss-Laguerre mode. Accordingly, one beamlet may be formed into a Gauss-Laguerre mode while another beamlet may be formed in a Gaussian mode. The utilization of Gauss-Laguerre modes greatly enhances trapping by reducing radiation pressure.

1. Imaging System

The current instrument design uses a high resolution CCD camera for the primary imaging system 110. The main advantage of the CCD camera (see reference numeral 511 in FIG. 5) is the favorable cost/performance ratio since this technology is a mature one. Another advantage of CCD cameras is their wide dynamic range and the ease of generating digital output.

The images are viewed on a computer screen (see reference numeral 510 in FIG. 5) to provide both a frame of reference for selecting the location of the traps as well as to minimize the possibility of inadvertent exposure of the operator to the laser.

2. User Interface a. Object Display

The user interface consists of a computer screen which displays the field of view acquired by the CCD camera. The user designates the loci of the traps with a mouse. There is also an option to delete a location.

As described in greater detail below, the user is also able to specify the power per trap so as to be able to avoid specimen damage. In addition it is desirable to be able to vary trap power because trapping depends upon the difference between the index of refraction of the specimen and the suspending medium which can be expected to vary from specimen to specimen.

b. The Hologram

The purpose of designating the loci of the traps is to provide input for the hologram calculation. The hologram is essentially a function whose Fourier transform produces the desired trap array. However in the case of the liquid crystal display this function is a phase object (i.e., an object that changes the phase of the wavefront without absorbing any energy).

c. Methods for Choosing the Set of Traps

Often one wishes to use the traps to move an object in a particular direction. This may be accomplished by using the mouse to create a line (by dragging). The computer program interprets a line as calling for a series of traps to be deployed sequentially and sufficiently close together so as to move the target in small steps without losing the lock on the target.

The present invention also includes the capability of changing the height of the traps. If a laser beam is parallel to the optical axis of the objective lens 409, then a trap forms at the same height as the focal plane of the lens 409. Changing the height of a trap is accomplished by adjusting the hologram so that the beam of light forming a trap is slightly converging (or diverging) as it enters the objective lens 409 of the microscope. Adjusting the height of a trap is possible using lenses but only a holographic optical trapping (HOT) allows the height of each individual trap to be adjusted independently of any other trap. This is accomplished by the computer program adjusting the phase modulation caused by the liquid crystal hologram.

3. Sample Holder a. General

Figure 7A:
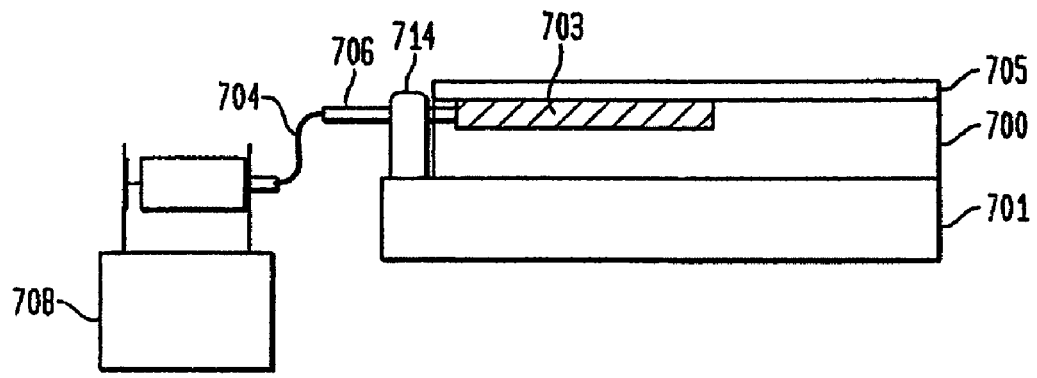
FIGS. 7A and 7B are a side (lateral) view schematic diagram and a top view schematic diagram, respectively, showing a sample being introduced into sample holder, in accordance with one embodiment consistent with the present invention.

The sample chamber 700 (see FIGS. 7A and 7B) of the present invention is inexpensive and disposable. Although the sample chamber 700 of the present invention is described below, another object of the present invention is to create a flexible design that may be changed for differing applications. In addition to the sample chamber 700, the various other separation stages of the invention may be utilized, such as an apparatus 100, 200 or 300, or the other separation stages discussed below with reference to FIGS. 13-24 and 26-27.

The sample chamber 700 lies on the surface of a microscope slide 701. The sample chamber 700 contains a series of channels 703 for introducing specimens or objects. The channels 703 are connected to supply and collection reservoirs by thin tubing 704 (commercially available). Samples or objects will be suspended in a liquid medium and will be introduced into the working area via the channels 703. The sample chamber 700 is covered by a cover slip 705.

b. Manufacture of the Sample Chamber

In one embodiment consistent with the present invention, a poly(dimethyl siloxane) (PDMS) resin is used to fabricate the chamber 700. The process involves creating the desired pattern of channels 703 on a computer using standard CAD/CAM methods and transferring the pattern to a photomask using conventional photoresist/etching techniques. The photomask is then used as a negative mask to create an inverse pattern of channels which are etched on a silicon wafer. The depth of the channels 703 is controlled by the etch time. The silicon wafer is a negative replica of the actual sample chamber 700. The final step consists of creating the positive sample chamber 700 by pouring PDMS onto the wafer and polymerizing. This results in a PDMS mold which is bonded to a glass slide 701 and overlaid with a cover slip 705. The glass to PDMA bonding is effected with an oxygen etch which activates the exposed surfaces.

A number of additional steps are necessary to ensure consistent quality. For instance the PDMS solution/hardener is maintained under a vacuum in order to prevent bubble formation. The silicon wafer is silanized to prevent the PDMS from sticking to the wafer. There are a variety of steps involving cleaning the replicas and maintaining proper environmental controls. These represent standard technology.

The channels 703 are connected to microbore tubing 704 using small syringe needles 706 held using glue 714, which are inserted through the PDMS mold into small circular wells 707 which connect to each channel 703. Sample solutions are introduced into the channel 703 using micropumps 708.

Figure 7B:
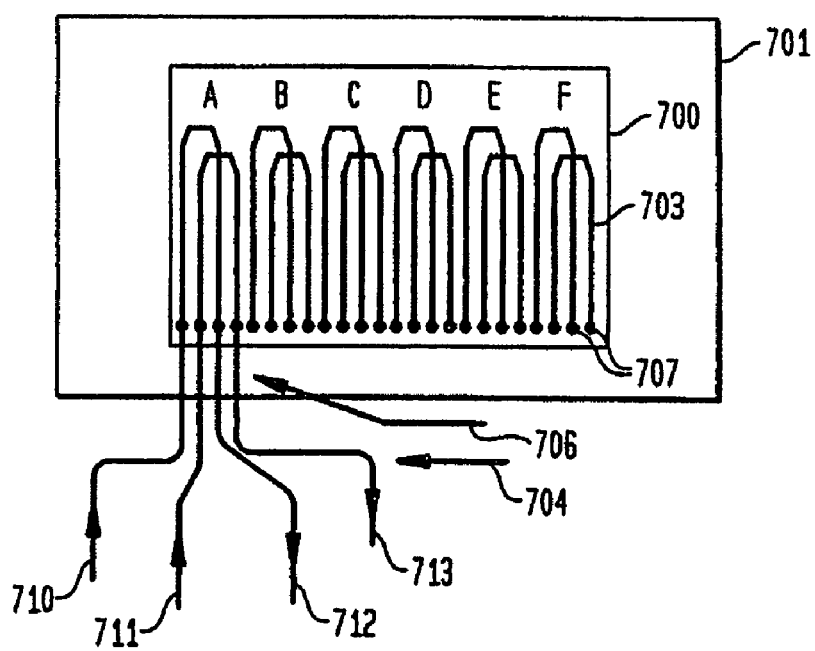

FIG. 7B shows a diagram of a typical arrangement for the introduction of a sample via the syringe pump 708 at 710. The medium is introduced at 711, and waste is collected at 71 and the desired collections at 713.

Figure 8:
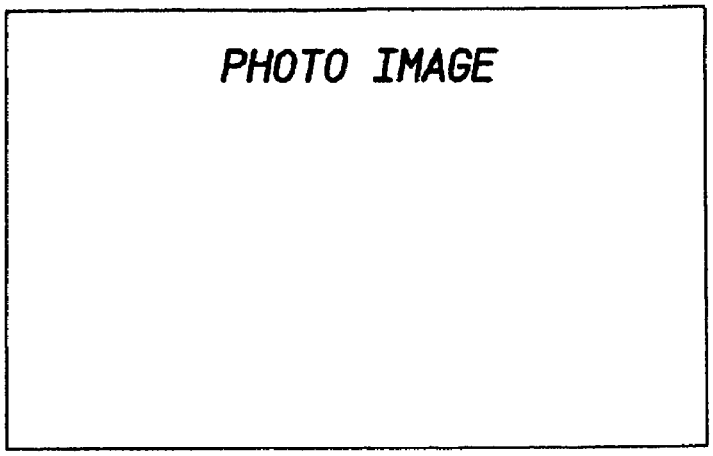
FIG. 8 depicts a scanning electron micrograph of a sample chamber in accordance with one embodiment consistent with the present invention.
Figure 9:
FIG. 9 shows an enlarged view of the working area of a sample chamber in accordance with one embodiment consistent with the present invention.

FIG. 8 presents a representation of a scanning electron micrograph of the diagram in FIG. 7B as actually created from the process described above. The channels are approximately 50 microns wide and 50 microns deep. FIG. 9 presents a representation of a scanning electron micrograph of the 'working' volume where manipulations of the specimen under study would occur. The diagrams clearly show that the channels 703 are smooth and clean. Although the channels 703 are rectangular in cross-section, other shapes may be devised as well. The channels 703 are designed to allow samples to be flowed to a 'working area' whose shape may be custom designed for experimental requirements.

c. Holographic Optical Traps

Unlike scanned optical traps which address multiple trapping points in sequence, and thus are time-shared, holographic optical traps illuminate each of their traps continuously. For a scanned optical trap to achieve the same trapping force as a continuously illuminated trap, it must provide at least the same time-averaged intensity. This means that the scanned trap has to have a higher peak intensity by a factor proportional to at least the number of trapping regions. This higher peak intensity increases the opportunities for optically-induced damage in the trapped material. This damage may arise from at least three mechanisms: (1) single-photon absorption leading to local heating, (2) single-photon absorption leading to photochemical transformations, and (3) multiple-photon absorption leading to photochemical transformations. Events (1) and (2) may be mitigated by choosing a wavelength of light which is weakly absorbed by the trapping material and by the surrounding fluid medium. Event (3) is a more general problem and is mitigated in part by working with longer-wavelength light. Thus holographic optical traps may manipulate delicate materials more gently with greater effect by distributing smaller amounts of force continuously among a number of points on an object rather than potentially damaging the object by exerting the total force on a single point or at a higher intensity for a period of time.

In one embodiment consistent with the present invention, the design is flexible in that any desired pattern of channels 703 may be designed with a standard CAD/CAM computer program. The complexity of the pattern is not a factor as long as the channels 703 are far enough apart so as not to impinge on one another. As may be seen in FIGS. 7B and 8, multiple sets of channels 703 may be easily accommodated so that a single chip may be used for more than one experiment. In addition, once a mold is made it may be used to fabricate thousands of sample chambers so the methodology is readily adaptable to mass production techniques. It is estimated that the marginal cost of a single chamber would be of the order of a few cents when in mass production.

4. Optical System a. Synthesizing the Hologram

Early versions of the holographic optical traps used fixed holograms fabricated from a variety of materials. These were adequate to demonstrate the principle of using holograms to create up to several hundred traps. However the major shortcoming of these holograms was that they were static and it took hours to make a single hologram. With the advent of the hardware to create computer-driven liquid crystal displays capable of forming holograms many times per second, the use of optical traps as a dynamic device has become a practical reality. Software control permits automation of separation and trapping by simple implementation of programs to control laser beam steering. The principle for computing the hologram is described below.

b. The Microscope

The optical system 410 consists of a standard high quality light microscope. The objective is a high numerical aperture lens 409 coupled with a long working distance condenser lens. The high numerical aperture objective lens 409 is used for trapping. While the long working distance condenser lens may somewhat reduce the resolution in the images, it does not compromise trapping and provides extra space near the sample slide to accommodate plumbing and receptacles. The objects may be moved by holding them with traps and moving the stage of the microscope vertically or laterally.

In one embodiment consistent with the present invention, approximately 2 mW of laser power is employed to produce 200 microwatts at the trap. The power level available from a 2 W laser is adequate to create about 1000 traps. A green laser (532 nm) is used, but other wavelengths may also be used, including, for example, a far red laser to work with materials absorbing near the 532 nm value.

Trapping depends upon the refractive index gradient so that materials with refractive indices close to that of the surrounding medium need traps with higher power levels. In addition, the tolerance of materials to damage will vary with trap power, so it is desirable for the user to be able to control this parameter. The user may increase the power level in any particular trap using a 'power slider' displayed on the graphical interface.

c. The Liquid Crystal Hologram (Also Referred to as a Spatial Light Modulator or SLM)

The spatial light modulator 408 is essentially a liquid crystal array controlled by an electrostatic field which, in turn may be controlled by a computer program. The liquid crystal array has the property that it retards the phase of light by differing amounts depending upon the strength of the applied electric field.

Nematic liquid crystal devices are used for displays or for applications where a large phase-only modulation depth is needed (2Π or greater). The nematic liquid crystal molecules usually lie parallel to the surface of the device giving the maximum retardance due to the birefringence of the liquid crystal. When an electric field is applied, the molecules tilt parallel to the electric field. As the voltage is increased the index of refraction along the extraordinary axis, and hence the birefringence, is effectively decreased causing a reduction in the retardance of the device.

d. The Laser

Useful lasers include solid state lasers, diode pumped lasers, gas lasers, dye lasers, alexandrite lasers, free electron lasers, VCSEL lasers, diode lasers, Ti-Sapphire lasers, doped YAG lasers, doped YLF lasers, diode pumped YAG lasers, and flash lamp-pumped YAG lasers. Diode-pumped Nd:YAG lasers operating between 10 mW and 5 W are preferred. The preferred wavelengths of the laser beam used to form arrays for investigating biological material include the infrared, near infrared, visible red, green, and visible blue wavelengths, with wavelengths from about 400 nm to about 1060 nm being most preferred.

FIG. 5 is a schematic diagram of a holographic optical trapping system for sorting objects, and is used in conjunction with an apparatus 100, 200 or 300, according to one embodiment in accordance with the present invention. In one such embodiment; an optical trapping system 500 (see FIG. 5) (such as the BioRyx system sold by Arryx, Inc., Chicago, Ill.) includes a Nixon TE 2000 series microscope 501 into which a mount for forming the optical traps using a holographic optical trapping unit 505 has been placed. The nosepiece 502 to which is attached a housing, fits directly into the microscope 501 via the mount. For imaging, an illumination source 503 is provided above the objective lens 504 to illuminate the sample 506. In accordance with the present invention, the sample 506 is one of the separation stages of the apparatus 100, 200 or 300.

In one embodiment, the optical trap system 400 (see FIGS. 4 and 5) includes one end of the first light channel which is in close proximity to the optical element, and the other end of the first light channel which intersects with and communicates with a second light channel formed perpendicular thereto. The second light channel is formed within a base of a microscope lens mounting turret or "nosepiece". The nosepiece is adapted to fit into a Nixon TE 200 series microscope. The second light channel communicates with a third light channel which is also perpendicular to the second light channel. The third light channel traverses from the top surface of the nosepiece through the base of the nosepiece and is parallel to an objective lens focusing lens 409. The focusing lens 409 has a top and a bottom forming a back aperture. Interposed in the third light channel between the second light channel and the back aperture of the focusing lens is a dichroic mirror beam splitter 408.

Other components within the optical trap system for forming the optical traps include a first mirror, which reflects the beamlets emanating from the phase patterning optical element 401 through the first light channel, a first set of transfer optics 406 disposed within the first light channel, aligned to receive the beamlets reflected by the first mirror, a second set of transfer optics 407 disposed within the first light channel, aligned to receive the beamlets passing through the first set of transfer lenses, and a second mirror 408, positioned at the intersection of the first light channel and the second light channel, aligned to reflect beamlets passing through the second set of transfer optics and through the third light channel.

To generate the optical traps, a laser beam is directed from a laser 507 (see FIG. 5) through a collimator and through an optical fiber end 508 and reflected off the dynamic surface of the diffractive optical element 509. The beam of light exiting the collimator aid of the optical fiber is diffracted by the dynamic surface of the diffractive optical element into a plurality of beamlets. The number, type and direction of each beamlet may be controlled and varied by altering the hologram encoded in the dynamic surface medium. The beamlets then reflect off the first mirror through the first set of transfer optics down the first light channel through the second set of transfer optics to the second mirror; and are directed at the dichroic mirror 509 up to the back aperture of the objective lens 504, are converged through the objective lens 504, thereby producing the optical gradient conditions necessary to form the optical traps. That portion of the light which is split through the dichroic mirror 509, for imaging, passes through the lower portion of the third light channel forming an optical data stream (see FIG. 4).

Spectroscopy of a sample of biological material may be accomplished with an imaging illumination source 503 suitable for either spectroscopy or polarized light back scattering, the former being useful for assessing chemical identity, and the later being suited for measuring dimensions of internal structures such as the nucleus size. Using such spectroscopic methods, in some embodiments, cells are interrogated. A computer 510 may be used to analyze the spectral data and to identify cells bearing either an X or Y chromosome, or a suspected cancerous, pre-cancerous and/or non-cancerous cell types, or identify various types of blood cells, for example. The computer program then may apply the information to direct optical traps to contain selected cell types. The contained cells then may be identified based on the reaction or binding of the contained cells with chemicals.

The present method and system lends itself to a semi-automated or automated process for tracking the movement and contents of each optical trap. The movement may be monitored, via video camera 511, spectrum, or an optical data stream and which provides a computer program controlling the selection of cells and generation of optical traps.

In other embodiments, the movement of cells is tracked based on predetermined movement of each optical trap caused by encoding the phase patterning optical element. Additionally, in some embodiments, a computer program is used to maintain a record of each cell contained in each optical trap.

The optical data stream may then be viewed, converted to a video signal, monitored, or analyzed by visual inspection of an operator, spectroscopically, and/or video monitoring. The optical data stream may also be processed by a photodetector to monitor intensity, or any suitable device to convert the optical data stream to a digital data stream adapted for use by a computer.

In an approach which does not employ an SLM (spatial light modulator), movement is accomplished by transferring the objects from a first set of optical traps to a second, third, and then fourth etc. To move the objects from the first position to a second position, a static phase patterning optical element is rotated around a spindle to align the laser beam with a second region which generates the second set of optical traps at a corresponding second set of predetermined positions. By constructing the second set of optical traps in the appropriate proximity to the first position, the probes may be passed from the first set of optical traps to the second set of optical traps. The sequence may continue passing the probes from the second set of predetermined positions to a third set of predetermined positions, from the third set of positions to a fourth set of predetermined positions, and from the fourth set of predetermined positions and so forth by the rotation of the phase patterning optical element to align the appropriate region corresponding to the desired position. The time interval between the termination of one set of optical traps and the generation of the next is of a duration to ensure that the probes are transferred to the next set of optical traps before they drift away.

In a staggered movement of the objects from a wide to narrow proximity the staggered movement of the cells occurs in a similar fashion. However, as the objects are passed from a first set of optical traps to a second set and moved to second and subsequent positions, the staggered arrangement of the traps allows the objects to be packed densely without placing a set of traps in too close a proximity to two objects at the same time which could cause the objects to be contained by the wrong optical trap.

Once an object or cell has interacted with a trap, spectral methods may be used to investigate the cell. The spectrum of those cells which had positive results (i.e., those cells which reacted with or bonded with a label) may be obtained by using imaging illumination such as that suitable for either inelastic spectroscopy or polarized light back scattering. A computer may analyze the spectral data to identify the desired targets and direct the phase patterning optical element to segregate those desired targets. Upon completion of the assay, selection may be made, via computer and/or operator, of which cells to discard and which to collect.

Optical peristalsis (see FIG. 13) is an existing process employing parallel lines of traps 1300 in a microfluidic channel 1301 arranged so that the spacing between the lines permits particles 1302 trapped in one line to be pulled into traps in the other line when the first line of traps is turned off. Optical peristalsis may be used as an alternative to and in conjunction with fluorescent labels (as described later regarding Applications). The process operates by timing the extinction of lines of traps timed so that particles are moved in desired directions specified by the arrangement of the lines of traps. By choosing whether a line of traps on one side or the other of a particle are on or off, the particle may be moved forward or back in a direction. By employing large numbers of traps, large numbers of particles may thus be moved in concert in a given direction. Thus, particles attracted to the traps may be moved to a given area and, if desired, collected there. This process may also be utilized in the various fluid flows utilized with the apparatus 100, 200 or 300.

Similarly, by gradually reducing the spacing between traps in lines toward a given direction and/or varying the curvature of the lines of traps, particles may be swept into a focusing pattern to concentrate them. Reversing such a pattern would disperse the particles.

Spacing between lines of traps may be relatively larger to speed up movement of the particles, or relatively narrower to slow them down. Similarly, varying the intensity of selected traps or lines, and hence their effect on particles, may also be employed. By converging or diverging flows, particles may be combined or separated. In addition, optical peristalsis may be combined with differential effects of viscous drag or electrical fields to produce complex and specific sets of parameter values for finely separating materials, for example. By opposing the trapping and other forces, the balance point of the two forces determines whether a particle moves with the trap or the other force.

In one embodiment consistent with the present invention, optical peristalsis may be implemented with a holographic system which cycles through a sequence of phase patterns to implement a corresponding sequence of holographic optical trapping patterns. Such patterns may be encoded in the surface relief of reflective diffractive optical elements mounted on the face of a prism, wherein each pattern is rotated into place by a motor. Likewise, transmissive diffractive optical elements may be placed on the perimeter of a disk and rotated to cycle through the patterns. Switchable phase gratings and phase holograms encoded on film may also be used.

For particles driven past a rectilinear array by an external bias force, such as fluid flow, where the trapping force is considerably greater than the external driving force, the particles are trapped. Where the bias force is greater, the particles flow past the array. Between these extremes, the bias force exceeds the trapping force to a differing degree for different fractions of the particles, causing the particles to hop from trap to trap along the direction of the principal axis of the array. A zero net deflection may be observed where the array is rotated to 45° because: (1) positive and negative displacements occur with equal probability; or (2) the particles become locked into the [11] direction, jumping diagonally through the array.

Particles affected to a greater degree by an array may be deflected to greater angles than the particles affected to a greater degree by the bias force. The optical gradient force exerted on particles varies roughly as $a^3$, where a=radius. Stokes drag on the particles varies as "a". Thus, larger particles are disproportionately affected by trap arrays, while the smaller particles experience smaller deflection. Orienting the array near the angle of optimal deflection and adjusting the intensity to place the largest particles in the hopping condition, and, hence at greater deflection than smaller particles. Differentially deflected particles may be collected or further fractionated by additional arrays downstream of the first.

Some conventional techniques for fractionation achieve separation in the direction of an applied force. However, such techniques operate on batches of samples rather than continuously.

Other conventional techniques for microfractionation employ microfabricated sieves consisting of a two dimensional lattice of obstacles or barriers. For example, an asymmetric placement of barriers rectifies the Brownian motion of particles that pass through the sieve, causing the particles to follow paths that depend on the diffusion coefficients of the particles. However, use of a microfabricated lattices clog and are not tunable for particle size and type.

Figure 10:
FIG. 10 illustrates an example of lateral deflection for sorting in accordance with one embodiment consistent with the present invention.

In FIG. 10, an example of sorting of particles according to the present invention is exemplified. Although the illustrated example exemplifies lateral deflection, optical peristalsis may be obtained in the same system. A representation of a video image shows light-based separation of material, in this case, tuned to separate objects based on particle size. The flow in the upper left channel contains 1, 2.25, and 4.5 µm particles and another flow enters from the lower left. The superimposed lines respectively indicate each of the channels' flow when the system laser power is off. When the laser power is turned on, light in the interaction region (indicated by the superimposed green box), extracts the 4.5 µm particles from the upper flow and delivers them to the lower-right channel as indicated by the superimposed white path.

6. Application in Blood Cell Sorting a. Background

In one application consistent with the present invention, a high-resolution, high-throughput cell sorter by using optical trapping technology is implemented. The need for implementing this technology as a new basis for cell sorting is evidenced by the failure of traditional flow cytometers to perform the high-resolution determinations of cell characteristics necessary in many sorting problems.

b. Sorting Using Holographic Optical Traps

The method of implementing high-resolution, high-throughput cell sorting of the present invention, has the following components: microfluidic development, optical-trap system development (trapping component for the funnel system and the trap component for the separation system), high-resolution fluorescence measurement, system control (including hologram calculation), and mechanical design.

Figure 11B:
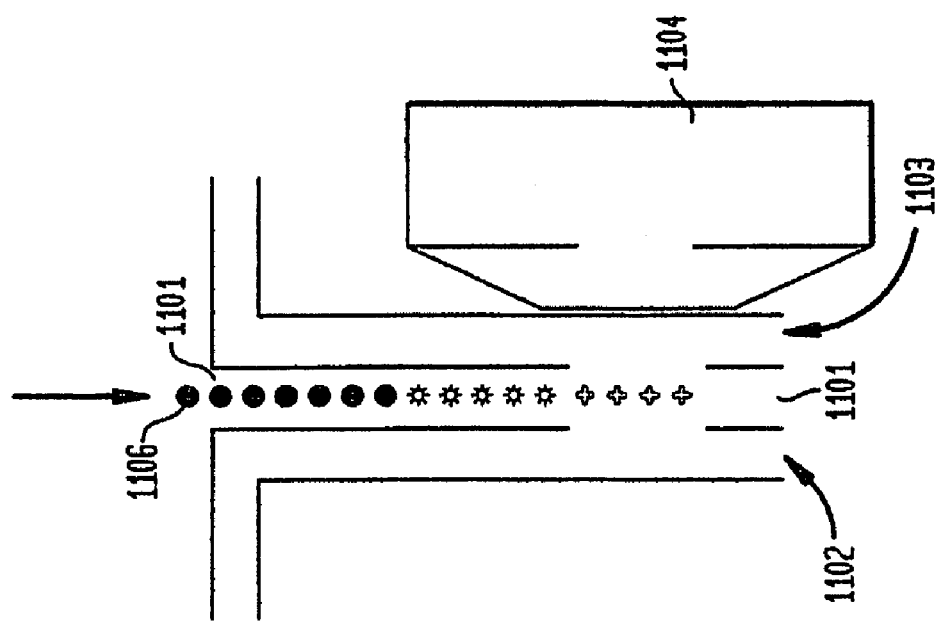
FIGS. 11A and 11B illustrate schematic front and side views, respectively, of the funneling traps in accordance with one embodiment consistent with the present invention.
Figure 11A:
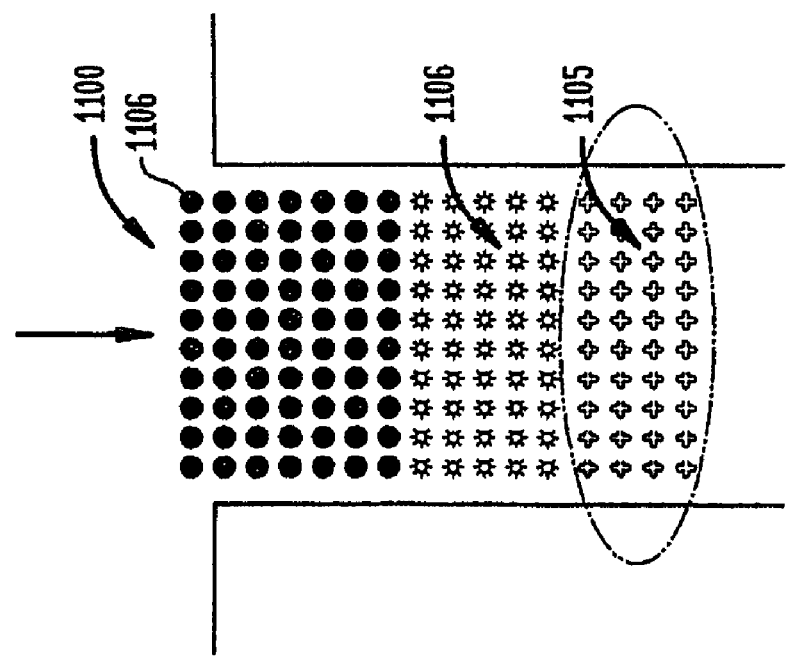

The first component is a flow cell that has a fluid input channel, carrying the input sample, and two output channels carrying cells separated out of the input channel. The second component is a set of traps that perform the "funneling" function (this "funneling function" is the equivalent of the nozzle forming the droplet flow in a traditional flow cytometer). The third component is the detection system and, finally, the fourth component is the sorting system. FIGS. 11A-11B illustrate the relationship among these four components. Similar functions can be implemented with the fluid flows utilized with the apparatus 100, 200 or 300.

The essential trait allowing this proposed embodiment of the present invention to achieve high throughputs is its inherent capacity to run material in parallel lines simultaneously and in close proximity to one another. For this initial implementation, a flow system with 10 input lines 1100 each separated by 10 microns is created. This sets an overall width to the flow from the input reservoir of 110 microns. The output channels 1102, 1103 are each the same 110 micron width as the input channel 301 and they run parallel to the input channel 301 as is shown in FIGS. 11A and 11B. Introduced into the "output channels" 1102, 1103 is a buffer solution that is fed into these channels at the same flow rate as is maintained in the input channel 1101. All three of these channels 1101, 1102, 1103 are designed to maintain laminar flow over the flow ranges of interest. The sorting stages discussed above with respect to the apparatus 100, 200 or 300 may also be utilized. In the sorting region, where specific cells are transferred from the input channel 1101 to one of the output channels 1102, 1103, all three flows are adjacent with no mechanical separation between them. The laminar flows keep any material in their respective flows unless a specific external force is introduced to transfer that material from one flow channel to another.

The funneling traps 1105 act on the input cells 1106 so they both travel in well defined lines of flow and so the input cells 1106 are separated from one another by a minimum distance 1106 to be set by the operator. The flow rates in the channels 1101, 1102, 1103 are set by this minimum distance 1106, by the "update" rate of the device that is performing the separation function, and by the overall cell processing rate desired.

The funneling system is composed of a pattern of low intensity traps 1105 established by a set of static holograms that are mounted in a rotating wheel so that the pattern changes as a function of the rotation pattern. The most down stream funneling traps are of fixed intensity and position, serving only to maintain the separation between the cells' lines of flow. The upstream traps 1105 are allowed to change both intensity and position with time to act so as to disturb the flow on clumped cells and pass through individual, or un-clumped, cells.

The measurement upon which the sorting determination is made may occur in the downstream region of the funneling traps 1105 or it may occur in a region further beyond the funneling system. For this initial system, the measurement will consist of high resolution fluorescence detection. In the future, however, other active sorting criteria may be implemented, such as scattering measurements, or passive techniques may be employed such as those using optical deflection as outlined earlier.

The final component of the device is the separation system in which the sorting criteria is utilized to divert cells into one of the output channels 1102, 1103 or to allow them to remain in the flow of the input channel 1101. The crucial parameter for this component is the field-of-view of the high-numerical-aperture objective lens 1104 used to implement the array of dynamic traps 1105 driving the separation. The width of this field-of-view is the same 110 microns as the individual channels' widths. The length, however, depends upon the flow rates, the channel depths, and the update rates of the optical device used to control these traps.

Currently, one embodiment consistent with the present invention includes spatial light modulators that create phase masks which are highly effective in driving optical trapping systems. These devices have update rates of 30 Hz or more. With an estimated channel depth of 10 microns, and assuming that the sperm cells should be moved in 1 micron steps, 10 updates of the spatial light modulator are employed to move a cell from the center of the input channel 1101 to the center of either output channel 1102, 1103. With an update value of 30 Hz, the implementation of these 10 steps will occur in ⅓ second. At a flow rate of 3 mm/second, these 10 steps are implemented on a length of 1 mm in the direction of flow. The objective lens 1104 for the separation component would therefore have a working area of 110 microns×1000 microns. An important development area of this project is the design of this lens assembly. The trade-off in lens design generally is between field-of-view and numerical aperture. That is, for a lens assembly of a particular complexity, a significant performance increase in one of these areas will come with a decrease in performance in the other area. It is for this reason that the high-performance lenses used in areas such as the high-resolution lithographic production of integrated-circuit electronics are quite complex. The present invention; however, does not require the full performance levels of these lens assemblies.

7. Disclosure on Wide-Field Vortex Tweezing

Tweezing with a wide field of view involves microscope objective lenses that have a relatively low numerical aperture. The ability to optically trap objects in the axial direction relies on focusing a light beam down in a manner that will have the largest gradients in the axial direction. This implies that a cone of light be formed with the broadest possible radius. The radius of the cone is directly determined by the numerical aperture of the objective, i.e., high numerical aperture means a broad cone radius. This is in direct conflict with the requirements for wide field of view. This has traditionally made tweezing with a wide field of view in the axial direction difficult. One of the major contributions to the difficulty in axial tweezing is the radiation pressure of the focused light beam. Especially for particles that are well matched in density to the surrounding medium, for example polystyrene microspheres, radiation pressure may blow particles out of the trap. With a low numerical aperture objective, it is difficult to overcome the radiation pressure with sufficient tweezing force in the axial direction. However, holographic optical traps have the ability to form exotic modes of light which greatly reduce the radiation pressure of the light beam. Vortex traps, for example, have a dark center because the varying phases of light cancel in the center of the trap. This dark center means most of the rays of light which travel down the center of the beam no longer exist. It is exactly these beams which harbor most of the radiation pressure of the light, so their removal greatly mitigates the difficulty in axial trapping. Other modes, e.g. donut modes; have the same advantage.

Manipulation (pushing, steering, sorting) of objects or cells in general, is made safer by having multiple beams available. Like a bed of nails, multiple tweezers ensure that less power is introduced at any particular spot in the cell. This eliminates hot spots and reduces the risk of damage. Any destructive two-photon processes benefit greatly since the absorption is proportional to the square of the laser power. Just adding a second tweezer decreases two-photon absorption in a particular spot by a factor of four.

Finally, manipulation of even just a single cell is greatly enhanced by utilizing holographic optical trapping. A single cell may be manipulated by a line of tweezers, which lift the cell along the perimeter on one side. The resulting rotation allows a 360 degree view of the cell. In addition to the advantage for viewing of biological samples, there also exists the ability to orient samples stably, which has clear benefit for studies such as scattering experiments which have a strong dependence on orientation of the sample.

8. Spinning Disk-Based Cell Sorter

The technology for using lasers to access a large number of sites quickly already exists in the form of a spinning laser disc, CD player, or DVD player. These devices combine rotational motion of the disc with radial motion of the laser to access sites with incredibly high speeds. For example, the typical DVD player may access approximately 4 billion separate "bits" on the disc in about two hours. Combining this spinning disc approach with optical trapping (see FIG. 12) allows access to cells at similar rates, and holographic optical trapping increases these rates by factors of 100 or even higher.

Figure 12:
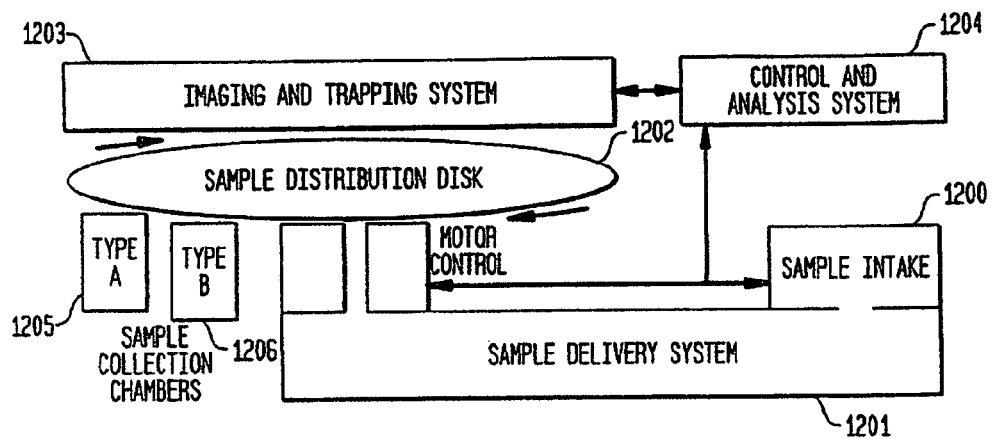
FIG. 12 illustrates a spinning disc-based cell sorter in accordance with one embodiment consistent with the inventions of the second and fifth related applications.
Figure 13:
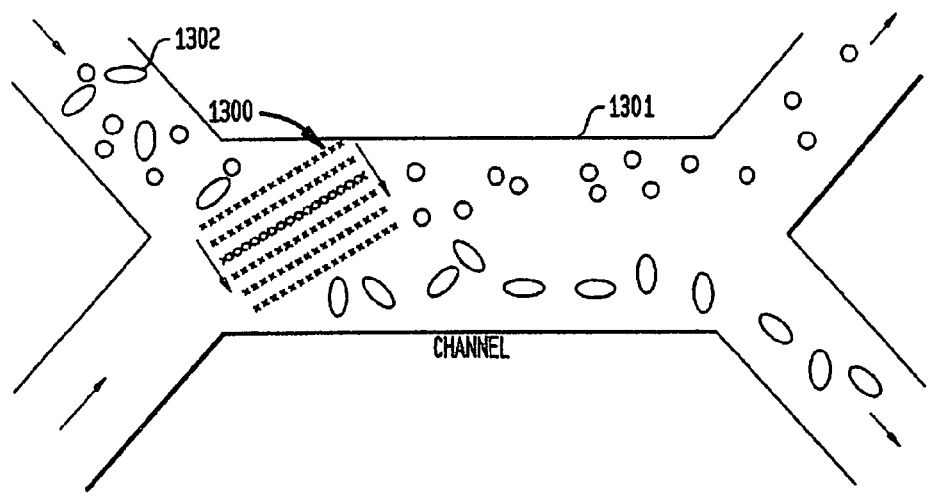
FIG. 13 illustrates optical peristalsis in accordance with one embodiment consistent with the present invention.

FIG. 12 illustrates a spinning disc-based cell sorter in accordance with one embodiment consistent with the inventions of the second and fifth related applications. As shown in FIG. 12, objects or cells are introduced at the sample intake 1200, and using an appropriate sample delivery system 1201, the cells are provided to the sample distribution disc 1202 which is rotated by a motor control. The imaging and trapping system 1203, which is connected to a control and analysis system 1204, sorts the cells and they are collected in sample chambers 1205 and 1206.

There are many mechanisms for distributing the cells over the surface of the disc. Fluid chambers which house individual cells, gels which immobilize the cells, sticky or waxy surfaces which bind the cells, or even freezing the cells into a solid mass, are all methods that may be employed. Once the cells are situated such that they maintain their relative positions, they may be appropriately measured. Optical trapping may then be used to free either the desired or unwanted cells from the surface or volume. In situations where sorting into more than two groups is desired, each group may be released in a single pass, and multiple passes may be executed.

9. Sorting of Cells and Non-Biological Material Using Meltable Substrates

Technologies such as Fluorescence-Activated Cell Sorting (FACS), although well-established, suffer from the fact that they are serial processing methods. Because of the ubiquity of labeling dyes in biology, sorting on the basis of these dyes is possible. These dyes often create a difference in absorption of some wavelength or range of wavelengths between dyed and undyed specimens, assuming that groups that are to be sorted do not already inherently exhibit such an absorption difference. Holographic optical traps may then be used to both heat and manipulate the specimen into a substrate which melts from the raised temperature of the specimen. The specimen which is embedded may then be released later with an increase in the bulk temperature. In addition, a faster, even more parallel processing method is possible in which the cells are illuminated by a broad, high power light source which processes the entire array of specimens simultaneously. The same set of methods may be applied to non-biological samples which differ in the absorption spectra, or may be selectively made to do so.

10. Gel-Based Sorting

Holographic optical laser traps construe a great advantage on the manipulation of objects in that they are able access and move objects in three dimensions. As biological sorting applications become more advanced, larger numbers of specimens need to be sorted, often in small amounts of time. The three-dimensional access of holographic optical traps means that these sorting applications may be realized. Quantities of cells and other specimens of biological interest which would be cumbersome or impossible to sort serially or on a two-dimensional substrate, may be effectively sorted.

One implementation of such three dimensional sorting relies on a reversible gelation process. The cells are gelled in a network, and then either wanted or unwanted cells are extracted from the gel using holographic optical traps. The heat from the traps may be used to melt the gel and provide exit pathways.

Alternatively, cells are selectively killed based on some criterion with the holographic optical laser traps. The entire gel is then melted and the live cells are separated from the dead. Instead of just killing, a more destructive thermal explosion may be generated, which disintegrates the cell into much smaller components, and then sorting on the basis of size may be effected, grouping or connecting certain cells together again.

11. Killing of Biological Specimens

A large variety of applications benefit from the ability to selectively kill biological specimens. Removing pathogens from blood is one such application. Cell sorting is another application. Cells are identified, one or more groups of cells are killed, and then the dead cells are removed. The killing is performed by the light energy from the lasers themselves, and do not necessarily require optical traps to perform this function.

Essentially, the cells are heated or the medium around the cells are heated with the laser beam, damaging and killing the cell. Holographic optical traps, because of their versatility and three-dimensional control, allow selective, massively parallel killing of cells.

12. Example

Using a BioRyx 200 System (Arryx, Inc., Chicago, Ill.) platelets may be tweezed from whole blood. The platelets tweeze at a low laser power (0.2 W) for 532 nm and they move easily in 3-D. It is preferable to use a slightly higher power for sending the platelets through automated traps, although 0.8 W is sufficient. Even in the presence of anti-coagulant, the platelets still have short strings of fibrin attached to them. Over long periods of time, the platelets may irreversibly bind to the cover slip. Platelets are roughly 2-3 micrometers in size, and they tweeze almost as well as 2-3 micron silica at 532 nm.

When the RBCs are in the same viewing frame as the platelets, they tend to be repelled by the out-of-focus light cone, even if the RBCs are well away from the traps. However, if the red blood cells come into contact with the laser, the laser will puncture them and often cause them to explode, depending on the osmolarity of the medium and the laser power. Different types of WBCs respond slightly differently to the laser tweezers. In general, WBCs are slightly repelled from them. Such differential responses to optical traps provide a basis for separating types of cells by their reaction to trapping beams. For example, platelets may be trapped and moved with steered laser beams while RBCs and certain WBCs are repelled and yet other WBCs are trapped and moved to an intermediate degree.

By combining techniques described above, it may be calculated that one may separate blood cell components at a rate of $10^{11}$ platelets per 20 minutes. Higher rates of sorting may be achieved by further combining these techniques with the laminar flow sorting of the apparatus 100, 200 or 300.

The various techniques described above may be used for sorting a wide variety of matter. For sorting sperm, for example, sperm may be sorted based upon motility or viability, such as by motile sperm moving or swimming into a selection stream, or by non-motile or nonviable sperm sedimenting into a waste stream. Sperm may also be sorted into multiple channels, each having different average motility. Sperm may also be isolated and separated from various pathogens or otherwise undesirable materials in the semen mixture. The separation described above may also be utilized for washing and/or cooling processes. In addition, yields or motile or viable sperm may be improved, for example, by manipulating the temperature of the various flows, and the chemical content of the flows, such as by adding attractants or repellants.

Figure 25:
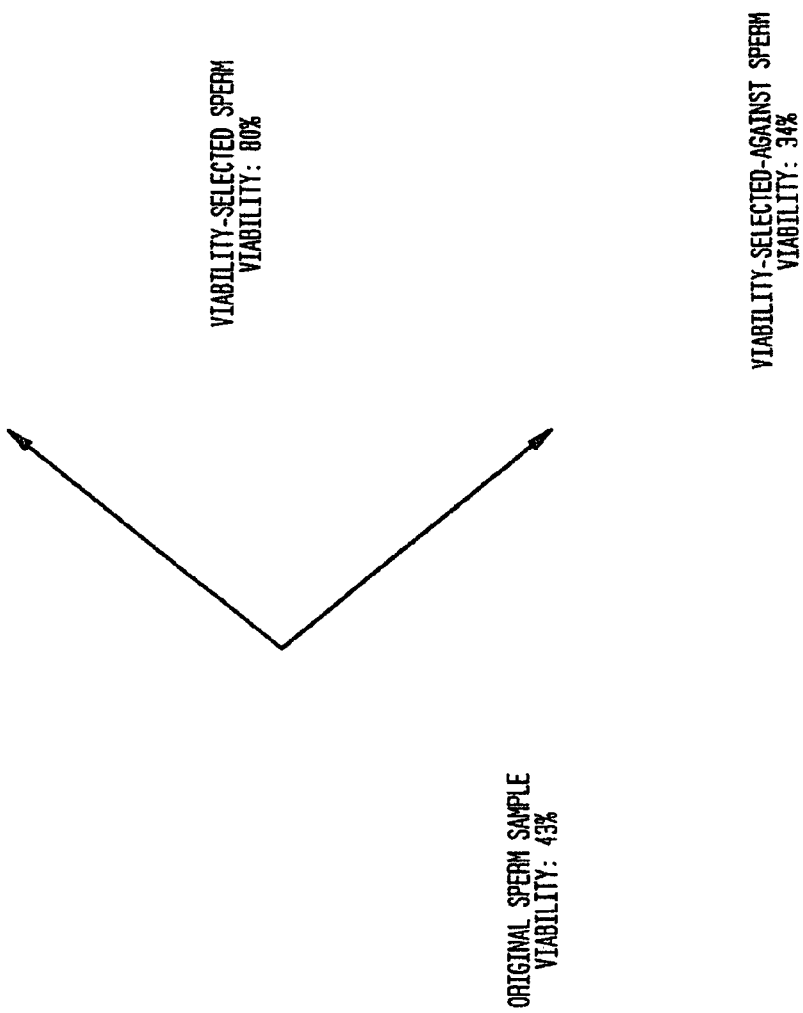
FIG. 25 illustrates the results of bovine sperm viability or motility sorting using the various embodiments of the present invention.

FIG. 25 illustrates the results of bovine sperm viability or motility sorting using the various embodiments of the present invention, in which a high motility and viability sample was generated from a lower viability and motility sample. Frozen sperm were thawed and rinsed in saline to remove glycerine, test yolk, and other materials, in order to provide density matching to the buffer solution or saline, PEG and BSA utilized in a second flow. Alternatively, glycerine may be added to the buffer flow). Flow rates of 0.01 to 0.1 ml/min were used, with 0.025 ml/min used most commonly, in a sorter such as the apparatus 200. Sperm concentrations of approximately 5 million with viabilities of 5-60% or higher were utilized as the input flow solution. Following sorting, the selected flow was found to have up to 80% viability, with results anticipated to approach 90-100% viability and motility.

Various other sorter configurations also may be utilized, and improved results may also occur through the use of laser steering in conjunction with the laminar flow-based sorting. For example, increasing buffer flow speed relative to input flow increases the width of the buffer channel in the separation region, decreasing the distance that sperm must move to enter the buffer flow (and increasing the distance to exit the buffer flow), increasing yield in the buffer flow (as the selected flow). Increasing the waste channel flow rate may also improve yield, forcing any dead sperm in the buffer layer near the input channel to be reintroduced into the waste channel.

The sorting described above may also utilize gradients to enhance sorting efficiency, with different flows having different properties, creating gradients such as, for example, temperature gradients, velocity gradients, viscosity gradients, and diffusion gradients.

In addition to sorting, the various embodiments of the invention may also be utilized to change concentrations of particles or cells, for example, such as increasing a concentration of particles in the selection stream, or diluting a concentration through an input buffer solution. Diffusion coefficients may also be manipulated, altering the diffusivity (or motility) of the objects in the various separation streams, such as through altering temperature, chemical concentrations, fluid viscosity, fluid density, salt concentrations, use of surfactants, etc. to, for example, alter the hydrodynamic radius or surface attraction of an object.

As a consequence, in accordance with the present invention, the plurality of holographic optical traps, which are capable of being independently manipulated, can be utilized in conjunction with an apparatus 100, 200 or 300, to manipulate components or particles, such as blood cells and other blood components, from one flow to another flow, as part of a separation stage. For example, components of interest in flow one may be identified and moved by the holographic optical traps into flow two, and thereby separated from the other components of flow one.

Figure 6A:
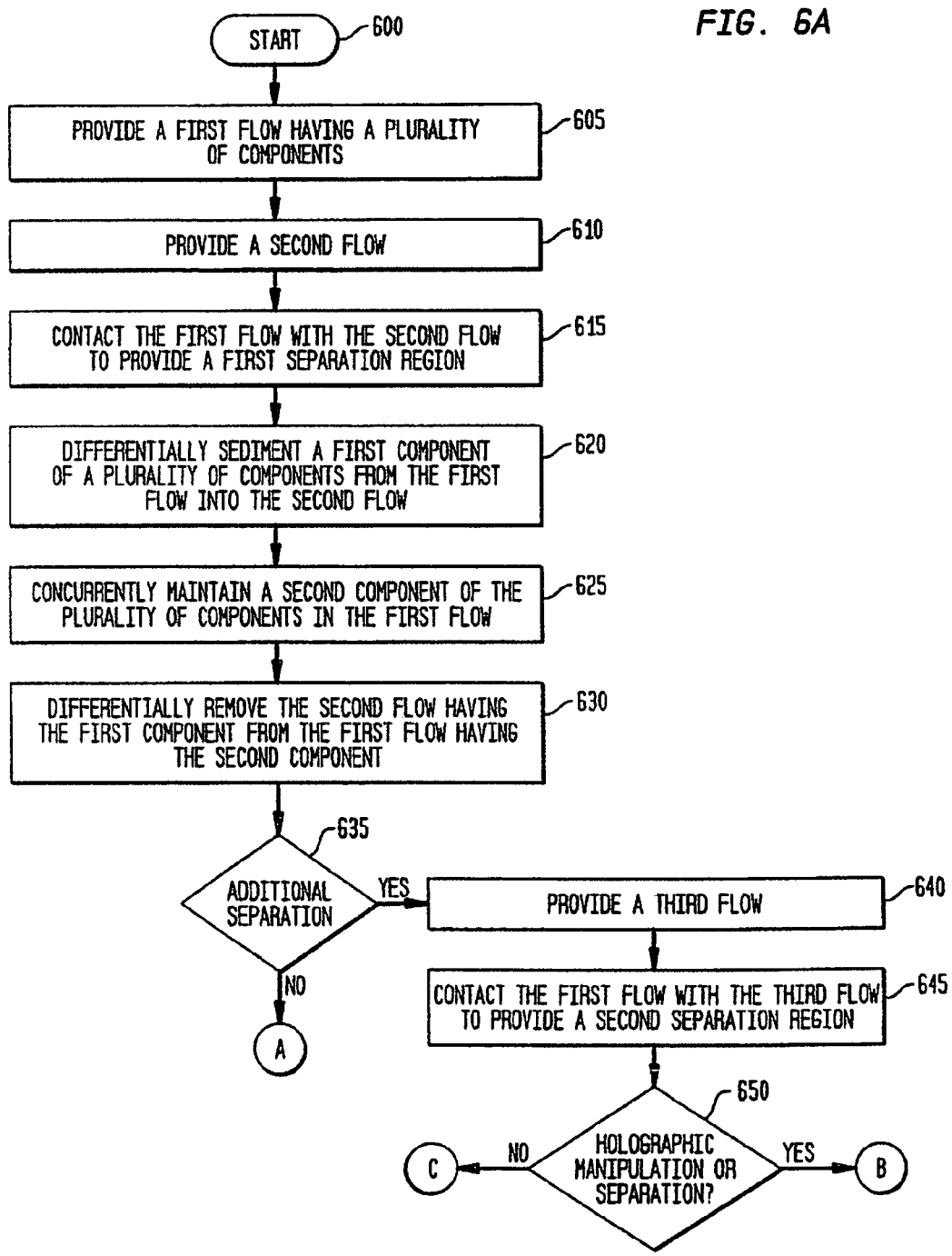
FIG. 6 (divided into FIG. 6A and FIG. 6B) is a flow diagram illustrating a method of consistent with the present invention.

FIG. 6 is a flow diagram illustrating a method embodiment of the present invention, and provides a useful summary. Beginning with start step 600, the method provides a first flow having a plurality of components, step 605, such as a plurality of blood components. A second flow is provided, step 610, and the first flow is contacted with the second flow to provide a first separation region, step 615. A first component of the plurality of components is differentially sedimented into the second flow, step 620, while a second component of the plurality of components is concurrently maintained in the first flow, step 625. The second flow having the first component is differentially removed from the first flow having the second component, step 630. When no additional separations (or stages) are to occur, step 635, the method may end, return step 680.

When an additional separation is to occur, step 635, the method proceeds to step 640, and a third flow is provided. The first flow is contacted with the third flow to provide a second separation region, step 645. When holographic manipulation is to be utilized in the second, additional separation, step 650, the method proceeds to step 655, and a plurality of holographic traps are generated, typically using optical wavelengths. Using the holographic traps, the second component of the plurality of components is differentially moved into the third flow, step 660. When holographic manipulation is not to be utilized in the second, additional separation, step 650, the method proceeds to step 665, and the second component of the plurality of components is differentially sedimented into the third flow. Following either step 660 or 665, a third component of the plurality of components is concurrently maintained in the first flow, step 670. The third flow having the second component is then differentially removed from the first flow having the third component, step 675, and the method may end, return step 680. While not separately illustrated in FIG. 6, it should be understood that the method may continue for additional separation stages, such as a third fourth, fifth, and so on.

Figure 14:
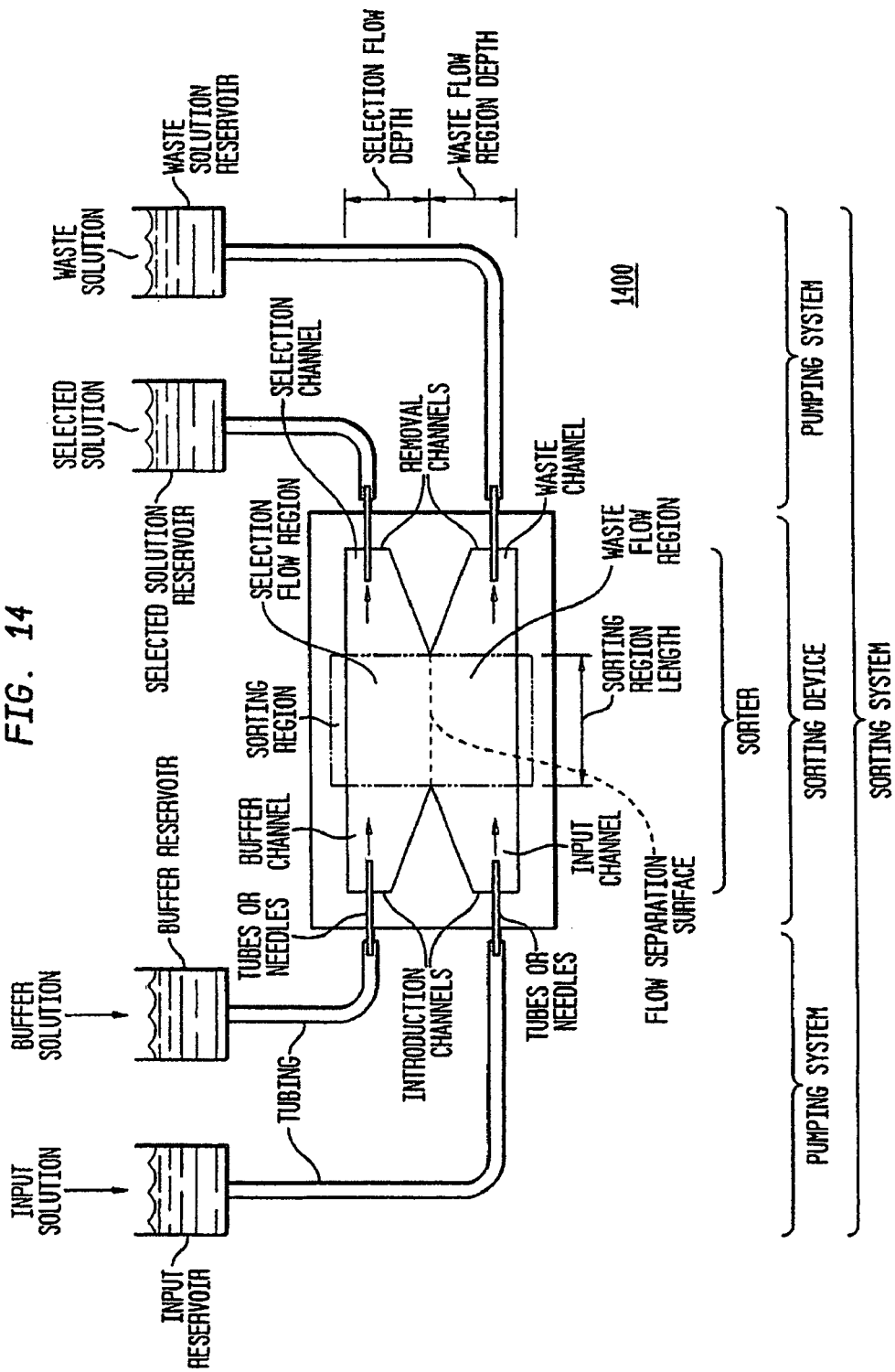
FIG. 14 illustrates a sorting system in accordance with one embodiment consistent with the present invention.
Figure 15:
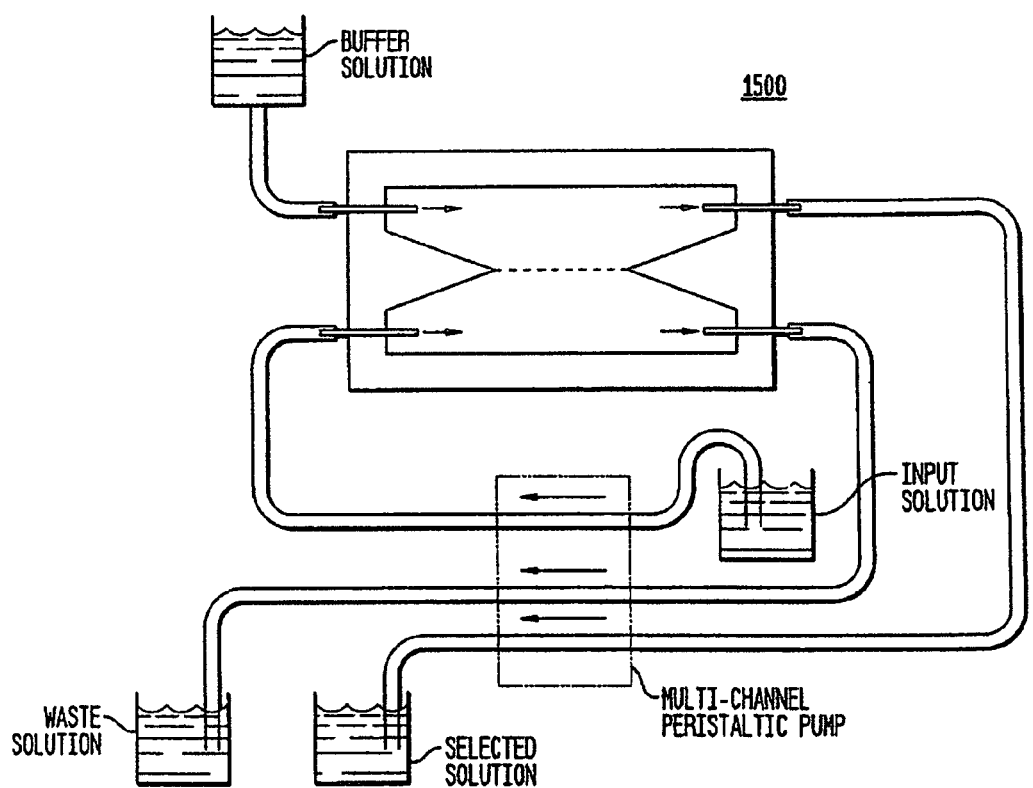
FIG. 15 illustrates a sorting system in accordance with one embodiment consistent with the present invention.
Figure 16:
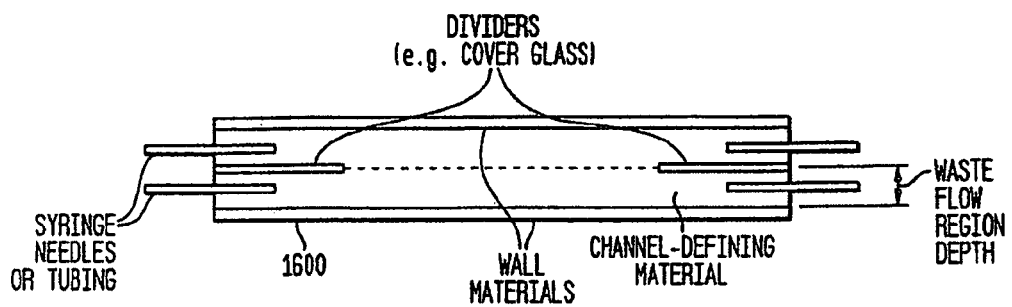
FIG. 16 is a lateral view of a high-aspect ratio flat sorter in accordance with one embodiment consistent with the present invention.
Figure 17:
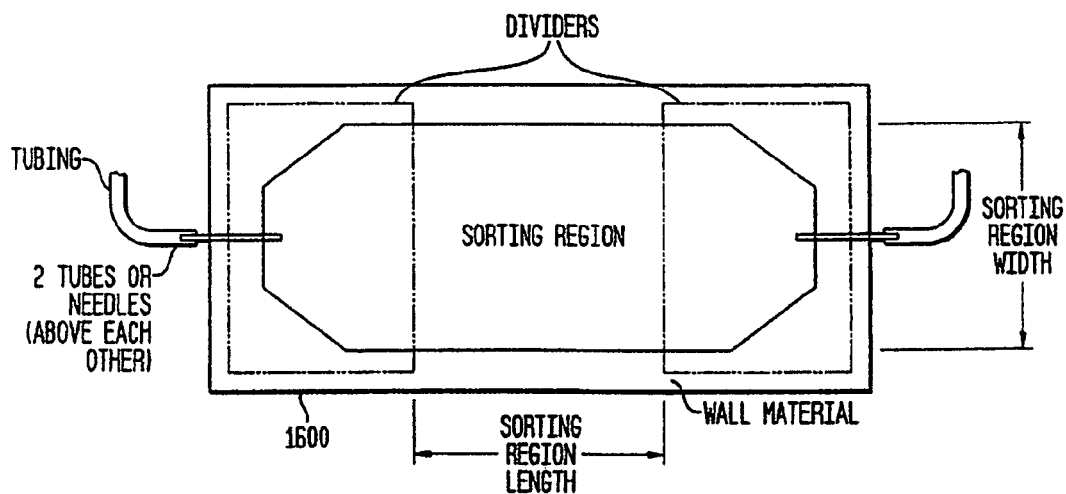
FIG. 17 is a plan view of a high-aspect ratio flat sorter in accordance with one embodiment consistent with the present invention.

Additional embodiments of the invention are illustrated in FIGS. 14-24. FIGS. 14 and 15 illustrate sorting systems 1400 and 1500 employing the various sorting stages of the apparatus 100, 200 or 300, including the use of reservoirs and peristaltic pumps for fluid flow. FIG. 16 is a lateral view and FIG. 17 is a plan view of a high-aspect ratio flat sorter 1600. Such high-aspect ratio sorters may be utilized to provide a comparatively large laminar flow separation surface between the various flows, providing a greater area of contact for component separation between the flows.

Figure 18:
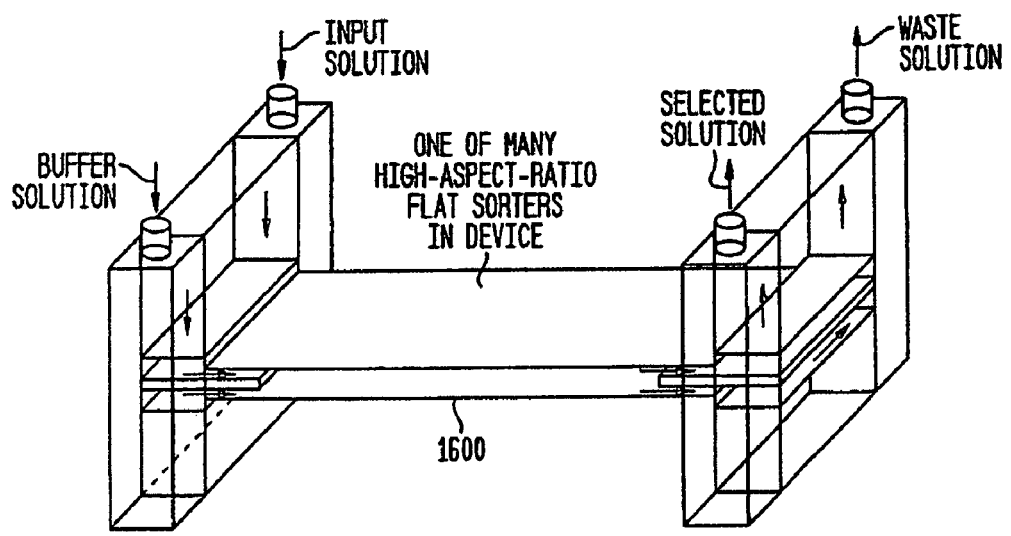
FIG. 18 is a perspective view of a three-dimensional sorting device having a plurality of flat sorters in accordance with one embodiment consistent with the present invention.
Figure 19:
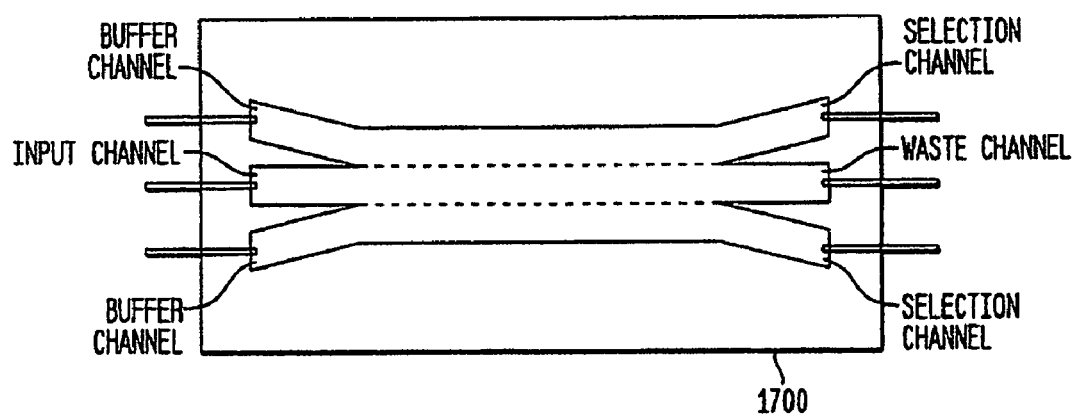
FIG. 19 is a plan view of a multi-channel sorter in accordance with one embodiment consistent with the present invention.
Figure 20:
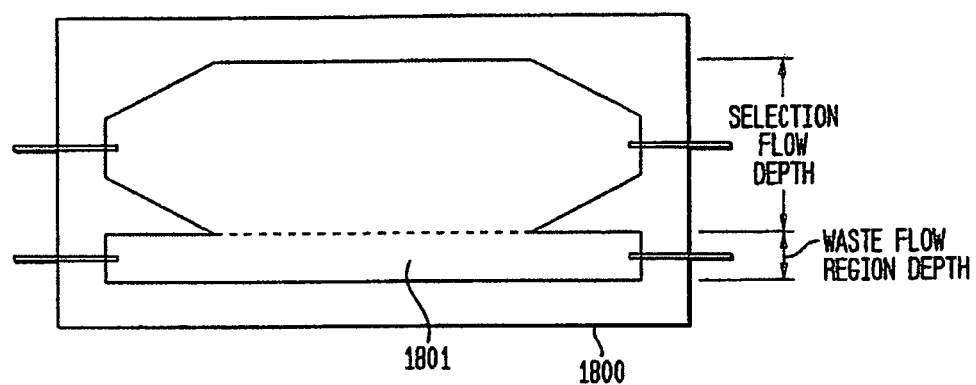
FIG. 20 is a plan view of a sorter having a narrow waste flow region in accordance with one embodiment consistent with the present invention.
Figure 21:
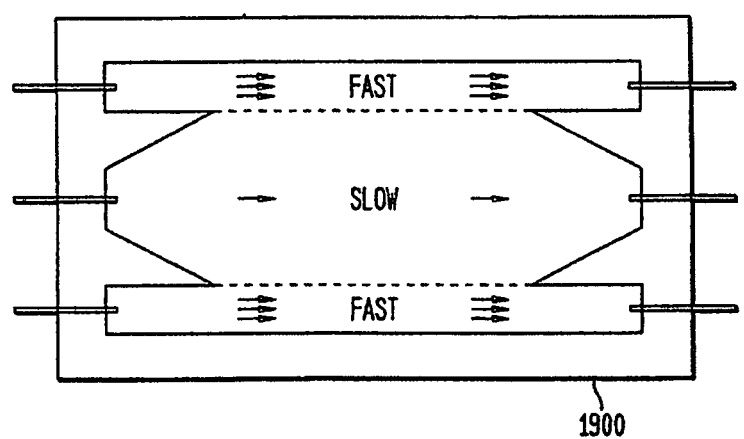
FIG. 21 is a plan view of a sorter using different flow rates for various channels in accordance with one embodiment consistent with the present invention.
Figure 22:
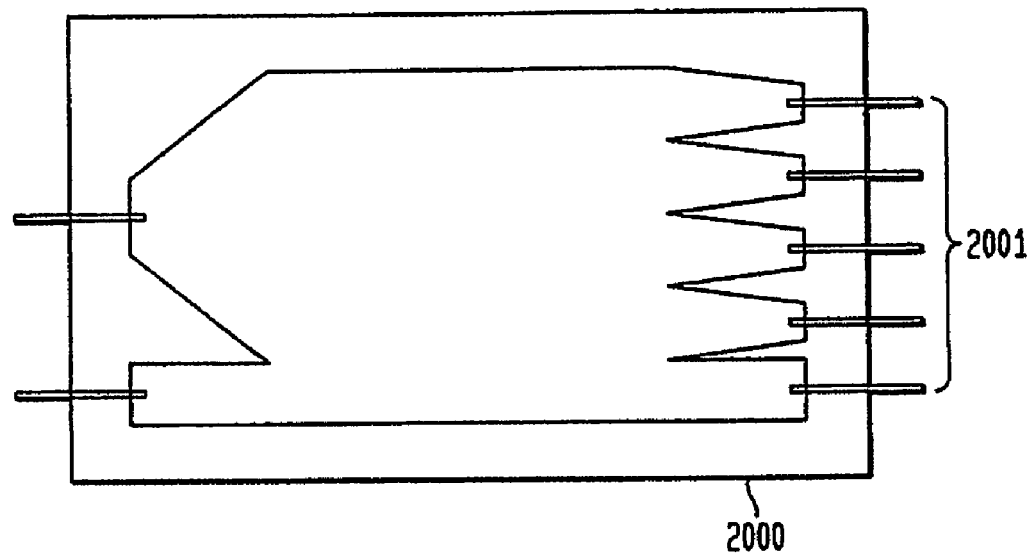
FIG. 22 is a plan view of a sorter having multiple selection channels in accordance with one embodiment consistent with the present invention.
Figure 23:
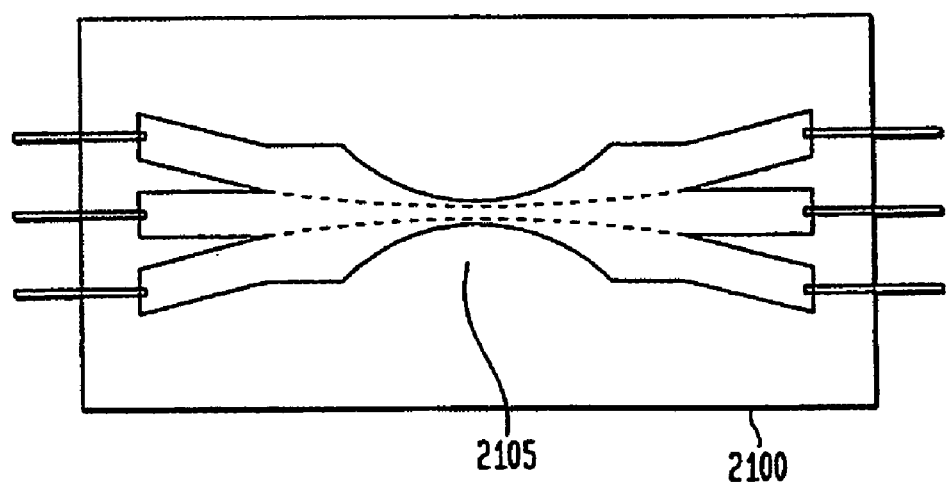
FIG. 23 is a plan view of a sorter having a constricted sorting region in accordance with one embodiment consistent with the present invention.

FIG. 18 is a perspective view of a three-dimensional sorting device having a plurality of flat sorters (with one illustrated, such as sorter 1600). FIG. 19 is a plan view of a multi-channel sorter 1700. FIG. 20 is a plan view of a sorter 1800 having a narrow waste flow region 1801. FIG. 21 is a plan view of a sorter 1900 using different flow rates for the various channels. FIG. 22 is a plan view of a sorter 2000 having multiple selection channels 2001. FIG. 23 is a plan view of a sorter 2100 having a constricted sorting region 2105.

Figure 24A:
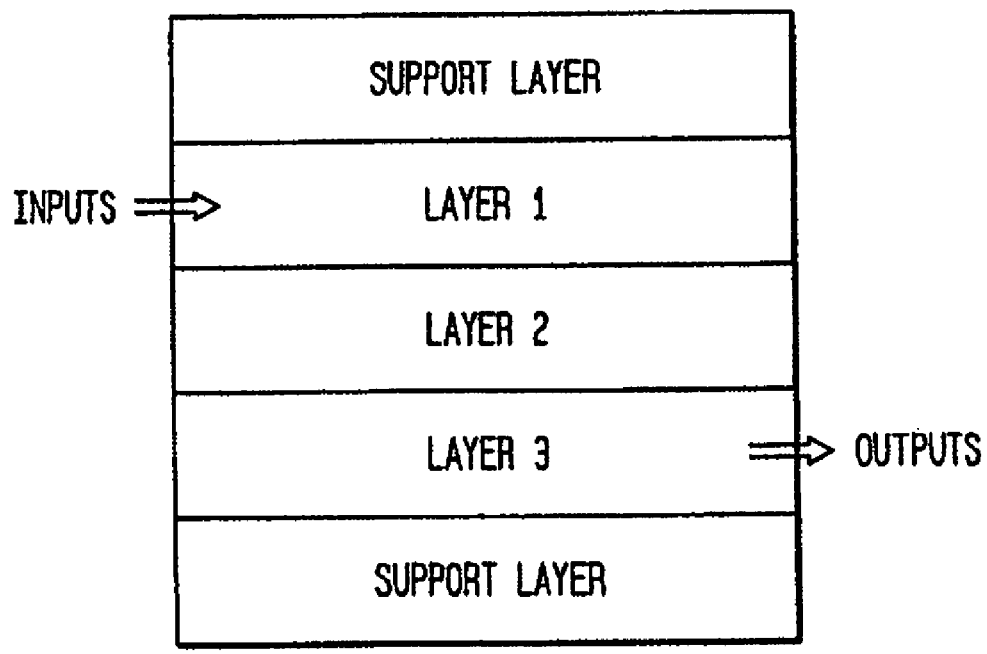
FIG. 24A is a lateral view of a multi-layer laminar flow sorter in accordance with one embodiment consistent with the present invention.

FIG. 24A is a lateral view and FIG. 24B is a plan view of a multi-layer laminar flow sorter 2200, with input channels in layer 1 (2210), layer 2 providing a plurality of sorting stages (2200), and layer 3 providing output channels (2230). These various sorting stages may also be connected in innumerable series and parallel connections. Numerous other variations of such a multi-stage sorter will be readily apparent to those of skill in the art.

Other shapes and configurations of channels may also be utilized. For example, a tortuous or "snake"-like channel configuration may be utilized to provide a longer interaction region in a small area or volume. Flow control posts may also be utilized in the separation region, to regulate the fluid flow in the channels. For example, vertical posts provide obstacles to fluid flow, effectively reducing channel size and the Reynolds number, and improving laminar flow.

Also in summary, and by way of example, the first component of the plurality of components may be a plurality of red blood cells and a plurality of white blood cells, while the second component is a plurality of platelets. In the second separation, the plurality of white blood cells may be holographically separated from the plurality of red blood cells, using techniques such as holographic (optical) trapping. Holographic trapping may also be utilized to holographically remove a plurality of contaminants from the first flow, or to holographically separate biological debris from the first flow. In the various embodiments, the first flow may substantially comprise whole blood from a donor and an anticoagulant, and the second flow may substantially comprise plasma from the donor. The various sedimentation steps may be rate zonal or isopycnic. The various flows are substantially non-turbulent, and may also be substantially laminar.

The first and second separation regions each have a predetermined length substantially parallel to a direction of flow and a predetermined depth substantially perpendicular to the direction of flow, the predetermined length and predetermined depth having been determined from a first sedimentation rate of the first component, from a second sedimentation rate of the second component, from a first flow rate of the first flow, and from a second flow rate of the second flow. The first flow and the second flow may have substantially the same flow rates. Alternatively, the first flow may have a first flow rate and the second flow may have a second flow rate, in which the second flow rate is comparatively greater than the first flow rate.

Also in summary, the present invention further provides an apparatus for separating a fluid mixture into constituent, non-motile components, including: (1) a first sorting channel (110 or 325) having a first inlet (120 or 315) for a first flow and a second inlet (120 or 320) for a second flow; the first sorting channel further having a first outlet (130 or the continuous channel of FIG. 3) for the first flow and a second outlet 130 (or 330) for the second flow, the first sorting channel adapted to allow a first component in the first flow, of a plurality of components in the first flow, to sediment into the second flow to form an enriched second flow and a depleted first flow, while concurrently maintaining a second component of the plurality of components in the first flow; (2) a second, optically transparent sorting channel (110 or 340) having a first optical inlet coupled to the first outlet (the continuous channel of FIG. 3) for the first flow and having a first optical outlet (350), the second, optically transparent sorting channel further having a second optical inlet (335) for a third flow and a second optical outlet for the third flow (345); and (3) a holographic optical trap system (400, 500) coupled to the second, optically transparent sorting channel, the holographic optical trap system adapted to generate a holographic optical trap to select and move the second component from the first flow into the third flow.

Another apparatus or system for separating a plurality of components in a fluid comprises: an optically transparent sorting channel 100, 200 or 300 having a first inlet for a first flow and a second inlet for a second flow, the optically transparent sorting channel further having a first outlet for the first flow and a second outlet for the second flow; and a holographic optical trap system coupled to the optically transparent sorting channel, the holographic optical trap system 500 adapted to generate a holographic optical trap to select and move a first component in the first flow, of a plurality of components in the first flow, into the second flow to form an enriched second flow and a depleted first flow, while a second component of the plurality of components is concurrently maintained in the first flow.

Lastly, another method embodiment provides for separating a plurality of cells, comprising: providing a first flow having the plurality of cells; providing a second flow; contacting the first flow with the second flow to provide a first separation region; and differentially sedimenting a first cell of the plurality of cells into the second flow while concurrently maintaining a second cell of the plurality of cells in the first flow. The method generally also includes differentially removing the second flow having the first cell from the first flow having the second cell. The method may also provide for providing a third flow; contacting the first flow with the third flow to provide a second separation region; and differentially sedimenting the second cell of the plurality of cells into the third flow while concurrently maintaining a third cell of the plurality of cells in the first flow. In addition, a plurality of second cells may be holographically separated from the first flow, and a plurality of contaminants or biological debris may be holographically removed from the first flow.

While discussion above has focused on the sorting of blood components to create different blood fractions, the apparatus, methods and systems of the present invention may be extended to other types of particulate, biological or cellular matter which are non-motile, which are capable of sedimenting or creaming within a fluid flow, or which are capable of being manipulated optically. For example, the methodology of the present invention could be utilized to separate non-motile or non-viable sperm cells from viable cells, by allowing the non-motile cells to sediment from a first flow into a second flow. Other sorts of cell separation may also be performed, such as separating islet cells from other types of pancreatic cells, or otherwise separating islet cell clusters of different sins, through either or both flow separation or optical tweezing (trapping). Viruses, proteins and other large molecules having different sedimentation rates may also be separated with the present invention. The holographic optical trapping utilized with the various separation stages may also be particularly useful in these other types of cell or particle separations.

From the foregoing, it will be observed that numerous variations and modifications may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

What is claimed is:

1. An apparatus for separating sperm cells containing X and Y chromosomes, comprising:
 a flow cell having a fluid input channel for introducing a sample of sperm cells having X and Y chromosomes employing a dye which binds to DNA, said sperm cells being in a laminar flow in said fluid input channel, said sperm cells being disposed in a plurality of input lines having a predetermined separation distance therebetween to determine a width of said fluid input channel;
 two output channels having a same width as said fluid input channel, said two output channels being disposed on either side of said fluid input channel, each having a buffer solution in a laminar flow flowing therethrough;
 a sorting region having no mechanical separation between said fluid input channel and said two output channels and said laminar flows therein;
 an optical trapping system which produces an array of a plurality of funneling optical traps in said fluid input channel proximate to said sorting region, said optical traps which separate said sperm cells in said fluid input channel by a minimum predetermined separation distance;
 wherein said optical trapping system includes a relatively high-numerical-aperture objective lens used to implement said array of optical traps driving separation of said sperm cells; and
 a fluorescence detection system, which detects fluorescence of said sperm cells, to determine a nature of an underlying chromosome load, to identify X from Y chromosomes of said sperm cells;
 wherein said X and Y chromosome bearing sperm cells are sorted in said sorting region.

2. The apparatus according to claim 1, wherein said sperm cells containing X and Y chromosomes are killed depending on a spectral analysis of an interrogation using a computer program.

3. The apparatus according to claim 2, wherein objects are killed by a laser beam.

4. The apparatus of claim 1, further comprising:
 a plurality of spaced apart regions or output channels, at least one of which receives the desired cells.

5. The apparatus of claim 4 wherein said fluid input channel, said plurality of input lines, and said two output channels are parallelized in said sorting region, within the flow cell.

6. The apparatus of claim 5, wherein said parallelization includes a multichannel arrangement of parallel input lines, and a plurality of additional output channels; and
 wherein said plurality of additional output channels are for said particles.

7. The apparatus of claim 6, wherein a flow rate of said particles in said fluid input channel is less than that of said particles in said two output channels.

8. A method of sorting sperm cells containing X and Y chromosomes, comprising:
 introducing a sample of sperm cells having X and Y chromosomes employing a dye which binds to DNA, into a laminar flow in a fluid input channel of a flow cell, said sperm cells being disposed in a plurality of input lines having a predetermined separation distance therebetween to determine a width of said fluid input channel;

introducing a buffer solution into a laminar flow into two output channels having a same width as said fluid input channel, said two output channels being disposed on either side of said fluid input channel;

providing a sorting region having no mechanical separation between said fluid input channel and said two output channels and said laminar flows therein;

producing an array of a plurality of funneling optical traps in said fluid input channel, proximate to said sorting region, using an optical trapping system, said optical traps which separate said sperm cells in said fluid input channel by a minimum predetermined separation distance;

wherein said optical trapping system includes a relatively high-numerical-aperture objective lens used to implement said array of optical traps driving separation of said sperm cells; and detecting a fluorescence of said sperm cells using a fluorescence detection system, to determine a nature of an underlying chromosome load, to determine X from Y chromosomes of said sperm cells;

wherein said X and Y chromosome bearing sperm cells are sorted in said sorting region.

9. The method according to claim 8, wherein said sperm cells containing X and Y chromosomes are killed depending on a spectral analysis of an interrogation using a computer program.

10. The method according to claim 9, wherein objects are killed by a laser beam.

11. The method of claim 8, further comprising:
parallelizing said fluid input channel, said plurality of input lines, and said two output channels, in said sorting region, within the flow cell.

12. The method of claim 11, wherein said parallelization includes a multichannel arrangement of parallel input lines, and said output channels; and
wherein said two output channels are for particles.

13. The method of claim 12, wherein a flow rate of said particles in said fluid input channel is less than that of said particles in said two output channels.

* * * * *